United States Patent
Gallardo Sánchez et al.

(10) Patent No.: US 10,087,200 B2
(45) Date of Patent: Oct. 2, 2018

(54) SILYLATED IMINE AND CARBAMATE POLYMERIC BENZOATE COMPOUNDS, USES, AND COMPOSITIONS THEREOF

(71) Applicant: Interquim, S.A., Barcelona (ES)

(72) Inventors: Adaya Gallardo Sánchez, Barcelona (ES); Santiago Nonell Marrugat, Barcelona (ES); Francisco Marquillas Olondriz, Barcelona (ES); Joan Sallares Rosell, Barcelona (ES); Ricardo Miralles Bacete, Barcelona (ES)

(73) Assignee: INTERQUIM, S.A., Barcelona (ES)

( * ) Notice: Subject to any disclaimer, the term of this patent is extended or adjusted under 35 U.S.C. 154(b) by 2 days.

(21) Appl. No.: 15/312,319

(22) PCT Filed: May 18, 2015

(86) PCT No.: PCT/EP2015/060837
§ 371 (c)(1),
(2) Date: Nov. 18, 2016

(87) PCT Pub. No.: WO2015/177064
PCT Pub. Date: Nov. 26, 2015

(65) Prior Publication Data
US 2017/0088567 A1    Mar. 30, 2017

(30) Foreign Application Priority Data

May 19, 2014  (EP) .................................. 14168778

(51) Int. Cl.
*C07F 7/18* (2006.01)
*A61K 8/02* (2006.01)
*A61K 8/58* (2006.01)
*A61Q 17/04* (2006.01)
*C08G 77/26* (2006.01)

(52) U.S. Cl.
CPC .......... *C07F 7/1836* (2013.01); *A61K 8/0241* (2013.01); *A61K 8/585* (2013.01); *A61Q 17/04* (2013.01); *C07F 7/1876* (2013.01); *C08G 77/26* (2013.01); *A61K 2800/412* (2013.01)

(58) Field of Classification Search
None
See application file for complete search history.

(56) References Cited

U.S. PATENT DOCUMENTS

| 4,328,346 A | 5/1982 | Chung et al. |
| 5,053,290 A | 10/1991 | Canivenc et al. |
| 5,089,250 A | 2/1992 | Forestier et al. |
| 5,618,520 A | 4/1997 | Hansenne et al. |
| 2008/0260664 A1 | 10/2008 | Walenzyk et al. |
| 2012/0230932 A1* | 9/2012 | Gallardo Sanchez ........... C07F 7/1836 424/60 |

FOREIGN PATENT DOCUMENTS

| EP | 0358584 A1 | 3/1990 |
| EP | 0392883 A1 | 10/1990 |
| EP | 0538431 B1 | 2/1996 |
| WO | WO 93/04665 A1 | 3/1993 |
| WO | WO 94/06404 A1 | 3/1994 |
| WO | WO 2005/053631 A1 | 6/2005 |
| WO | WO 2005/120440 A1 | 12/2005 |
| WO | WO 2006/100225 A2 | 9/2006 |
| WO | WO 2009/101016 A2 | 8/2009 |
| WO | WO 2011/045389 A1 | 4/2011 |

OTHER PUBLICATIONS

Extended European Search Report for European Application No. 14168778.0, dated Nov. 14, 2014.
International Search Report and Written Opinion of the International Searching Authority (Forms PCT/ISA/210 and PCT/ISA/237) for International Application No. PCT/EP2015/060837, dated Jun. 18, 2015.
Walenzyk et al., "Synthesis of Mono-Dispersed Spherical Silica Particles Containing Covalently Bonded Chromophores," International Journal of Cosmetic Science, vol. 27, 2005, pp. 177-189.

* cited by examiner

*Primary Examiner* — H. Sarah Park
(74) *Attorney, Agent, or Firm* — Birch, Stewart, Kolasch & Birch, LLP

(57) ABSTRACT

The present invention relates to organosilicon polymers containing benzoic acid esters in form of particles, process for their preparation, cosmetic or dermatological composition comprising them, as well as their use for protecting a human or animal living body from UV radiation.

14 Claims, 14 Drawing Sheets

SILYLATED IMINE AND CARBAMATE POLYMERIC BENZOATE COMPOUNDS, USES, AND COMPOSITIONS THEREOF

CROSS-REFERENCE TO RELATED APPLICATIONS

This application is the National Stage entry of PCT/EP2015/060837, filed on May 18, 2015, which claims priority to European Application Number 14168778.0, filed on May 19, 2014, which are incorporated herein by reference in their entireties.

TECHNICAL FIELD

This invention is directed to organosilicon polymers containing benzoic acid esters in form of particles to be used in topical preparations for affording protection against sunlight or other radiation.

BACKGROUND

There is a constantly increasing need for sunscreen protection agents in a population that is exposed to an increasing amount of damaging sunlight. The damage can be immediate and long-term, with effects ranging from sunburn, rashes, and cell and tissues damage to premature wrinkling and skin cancer. In this sense, many sunscreening chemicals have been developed in the past protecting against the harmful effect of UV-A and/or UV-B wavelength and even shorter wavelength. These chemicals are usually incorporated either alone or in combination with each other into cosmetic or pharmaceutical preparations which are widely known and used.

Most UV filters used in sunscreen compositions are monomeric compounds having the inherent risk that such compounds can penetrate the skin barrier, which is a highly undesirable effect. Thus, the major drawbacks derived from the use of common sunscreens are adverse reactions comprising cutaneous problems, such as allergic contact reactions, photocontact reactions, and drying or tightening of the skin. Subjective irritation associated with burning or stinging without objective erythema is the most common sensitivity complaint from sunscreens. This irritation is most frequently observed in the eye area. However, persistent objective irritant contact dermatitis is a more common side effect. Individuals with preexisting eczematous conditions have a significant predisposition to sensitization associated with their impaired cutaneous barrier. In addition, certain antibiotics, birth control pills, diuretics, antihistamines and antidepressants are among the commonly used drugs that can increase sensitivity to the sun's rays. Moreover, some of these cutaneous problems are induced by degradation products of the sunscreens formed upon exposure to sunlight. Attempts have been made to solve the risk of skin penetration by encapsulating at least one type of UV filter which is present in a sunscreen formulation. For example, UV filters on the basis of polysiloxanes which may be either linear or cyclic have been described in WO93/04665, WO94/06404, EP538431, EP392883 and EP358584. With these polysiloxanes the risk of skin penetration is lower, but it is sometimes difficult to incorporate the polysiloxanes in sunscreen compositions due to incompatibility problems. Patent application WO2005/053631 refers to microcapsules with UV filter activity, wherein at least one type of crosslinkable chromophore with UV-A and/or UV-B and/or UV-C filter activity, and optionally at least one type of crosslinkable monomer which has no UV-A and/or UV-B and/or UV-C filter activity, are subjected to a crosslinking reaction in the absence of non-crosslinkable chromophores with UV-A and/or UV-B and/or UV-C filter activity. The invention also refers to sunscreen compositions comprising said microcapsules.

The prior art also describes some UV absorbers in the form of particles. In this sense, patent application WO2005/120440 refers to particles comprising an inorganic network and organic compounds covalently bonded to the network via a spacer group, characterised in that the organic compounds are present in the interior of the particles and optionally also on the surface of the particles. The invention also refers to formulations and compositions comprising said particles.

Patent application WO2009/101016 and Walenzyk, T. et al., *International Journal of Cosmetic Science* (2005), 27(3), 177-189, refer to particles that can be obtained by the reaction of inorganic nanoparticles with organic molecules containing functional groups, and use thereof as UV absorbers in cosmetic or dermatological applications.

Some benzoic acid ester compounds have been discovered and disclosed in WO2006/100225, as well as their uses as photochemical precursors of ultraviolet absorbers, processes, cosmetic or pharmaceutical compositions, personal care compositions, and industrial compositions related thereto. Some silane-functionalized ultraviolet screening agent precursors have also been disclosed in U.S. Pat. No. 4,328,346. These compounds undergo a photochemical transformation in the presence of sunlight that enhances their UV screening ability.

Document WO2011/045389 describes some silyl polymeric benzoic acid esters compounds in the form of particles having an increased photostability and increased persistence on the skin as they have the relevant physical property of being essentially hermetic, thus avoiding the release of benzoic acid ester compounds and its phototransformation products, endowing with a safer profile both for sunscreen user and for the environment. However, the rate of conversion under the typical light doses under real solar irradiation conditions was not fast enough to provide the best protection to the users. In addition, the synthesis of some of these compounds required the use of harmful starting compounds, as well as expensive and long-lasting purification steps, and the yield is not good enough to allow the production thereof on an industrial scale. On top of that, the presence of standard UV filters in the sunscreen formulation resulted in low conversions for these compounds, which further detracted from their protection efficiency.

Thus, it is desirable to develop new sunscreen compounds with higher UV screening ability, faster conversion rates, ability to convert in the presence of additional UV filters, and that can be obtained by cost-effective and easier synthetic routes.

BRIEF DESCRIPTION OF THE INVENTION

The authors of the present invention have developed new mono-silylated polymeric benzoic acid ester compounds in the form of particles, useful as progressive photoprotective agents over UV radiation, which present the particular advantage of a faster and more efficient conversion even in the presence of standard UV filters in the final sunscreen preparation. This allows them to perform their progressive action despite the inner-filter effects provided by the regular filters, and therefore to compensate for the loss of protecting efficiency that commonly affects standard UV filters.

Contrary to other mono-silylated polymeric benzoic acid ester compounds of the prior art, the compounds of the invention are characterized for having the silylated chain attached to the acyl ring of the benzoic group, instead of to the phenyl ring of the ester group, and for the presence of an imine or a carbamate group as linker between the benzoic acid ester and said silylated chain.

In addition to that, these compounds can be synthesized from an aldehyde compound by means of a short synthetic route, with non-toxic stating compounds which are also affordable and cheap. This synthesis provides compounds with a higher purity and also higher yields at a lower manufacturing cost.

The polymers of the present invention also show a progressive UV protection depending on the time to sun exposition and the degree of sun radiation. Thus, compositions containing such compounds constitute a safer method to take sunbaths than conventional sunscreen products, since protection increases with time of sun exposition and the intensity of radiation.

The polymers of the invention exhibit ultraviolet absorbing properties per se and are susceptible to be photochemically converted in situ to another screen compound with a higher UV protection.

In a first aspect, the present invention refers to a process for the preparation of an organosilicon progressive photoprotective polymer, which comprises the reaction of a monomer of formula (I):

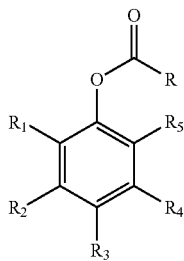

(I)

wherein:
R is selected from the group consisting of (i), (ii) and (iii):

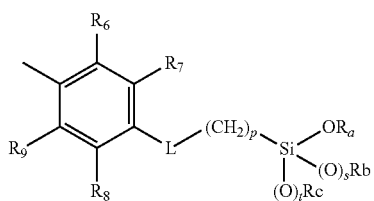

(i)

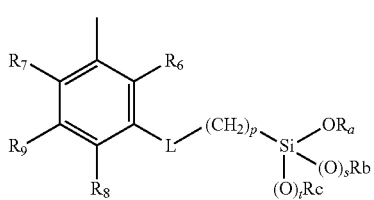

(ii)

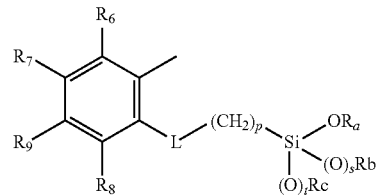

(iii)

wherein:
$R_1$, $R_2$, $R_3$, $R_4$ and $R_5$ are independently selected from the group consisting of H, linear or branched $(C_1\text{-}C_6)$alkyl, $(C_3\text{-}C_6)$cycloalkyl, $OR_{10}$, $NH_2$, $NHR_{11}$, $NR_{12}R_{13}$, COOH, $COOR_{14}$, $CONH_2$, $CONHR_{15}$, $CONR_{16}R_{17}$, $SO_2NH_2$, $SO_2NHR_{18}$, and $SO_2NR_{10}R_{20}$, with the proviso that at least one of $R_1$, $R_2$, $R_3$, $R_4$ and $R_5$ is not H provided that at least one of $R_1$ and $R_5$ is H;

$R_6$, $R_7$, $R_8$ and $R_9$ are independently selected from hydrogen, linear or branched $(C_1\text{-}C_6)$alkyl, $(C_3\text{-}C_6)$cycloalkyl, $OR'_1$, $NH_2$, $NHR'_2$ and $NR'_3R'_4$;

$R_{10}$ is linear or branched $(C_1\text{-}C_6)$alkyl or $(C_3\text{-}C_6)$cycloalkyl;

$R_{11}$ is linear or branched $(C_1\text{-}C_6)$alkyl or $(C_3\text{-}C_6)$cycloalkyl;

$R_{12}$ is linear or branched $(C_1\text{-}C_6)$alkyl or $(C_3\text{-}C_6)$cycloalkyl;

$R_{13}$ is linear or branched $(C_1\text{-}C_6)$alkyl or $(C_3\text{-}C_6)$cycloalkyl; or $R_{12}$ and $R_{13}$ taken together with the nitrogen atom to which they are attached form a pyrrolidine, piperidine or morpholine ring;

$R_{14}$ is linear or branched $(C_1\text{-}C_6)$alkyl or $(C_3\text{-}C_6)$cycloalkyl;

$R_{15}$ is linear or branched $(C_1\text{-}C_6)$alkyl or $(C_3\text{-}C_6)$cycloalkyl;

$R_{16}$ is linear or branched $(C_1\text{-}C_6)$alkyl or $(C_3\text{-}C_6)$cycloalkyl;

$R_{17}$ is linear or branched $(C_1\text{-}C_6)$alkyl or $(C_3\text{-}C_6)$cycloalkyl; or $R_{16}$ and $R_{17}$ taken together with the nitrogen atom to which they are attached form a pyrrolidine, piperidine or morpholine ring;

$R_{18}$ is linear or branched $(C_1\text{-}C_6)$alkyl or $(C_3\text{-}C_6)$cycloalkyl;

$R_{19}$ is linear or branched $(C_1\text{-}C_6)$alkyl or $(C_3\text{-}C_6)$cycloalkyl;

$R_{20}$ is linear or branched $(C_1\text{-}C_6)$alkyl or $(C_3\text{-}C_6)$cycloalkyl; or $R_{19}$ and $R_{20}$ taken together with the nitrogen atom to which they are attached form a pyrrolidine, piperidine or morpholine ring;

L is a linker selected from:
—CH=N—
—(CH$_2$)—O—C(O)—NH—

$R_a$ is linear or branched $(C_1\text{-}C_6)$alkyl, linear or branched $(C_2\text{-}C_6)$alkenyl, $(C_3\text{-}C_6)$cycloalkyl or phenyl;

$R_b$ is linear or branched $(C_1\text{-}C_6)$alkyl, linear or branched $(C_2\text{-}C_6)$alkenyl, $(C_3\text{-}C_6)$cycloalkyl or phenyl;

$R_c$ is linear or branched $(C_1\text{-}C_6)$alkyl, linear or branched $(C_2\text{-}C_6)$alkenyl, $(C_3\text{-}C_6)$cycloalkyl or phenyl;

$R'_1$ is linear or branched $(C_1\text{-}C_6)$alkyl or $(C_3\text{-}C_6)$cycloalkyl;

$R'_2$ is linear or branched $(C_1\text{-}C_6)$alkyl or $(C_3\text{-}C_6)$cycloalkyl;

$R'_3$ is linear or branched $(C_1\text{-}C_6)$alkyl or $(C_3\text{-}C_6)$cycloalkyl;

$R'_4$ is linear or branched $(C_1\text{-}C_6)$alkyl or $(C_3\text{-}C_6)$cycloalkyl; or $R'_3$ and $R'_4$ taken together with the nitrogen atom to which they are attached form a pyrrolidine, piperidine or morpholine ring;

p is an integer selected from 2, 3 and 4;

s is an integer selected from 0 and 1;

t is an integer selected from 0 and 1;

with a compound of formula (IV):

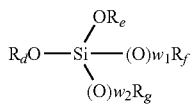
(IV)

wherein:

$R_d$ is a linear or branched $(C_1-C_6)$alkyl;

$R_e$, $R_f$ and $R_g$ are independently a linear or branched $(C_1-C_6)$alkyl, linear or branched $(C_2-C_6)$alkenyl, $(C_3-C_6)$cycloalkyl or phenyl, $w_1$ and $w_2$ are independently 0 or 1, in an alkanol/water mixture.

In a second aspect, the present invention refers to an organosilicon progressive photoprotective polymer obtainable by a process as defined above, characterised in that it exhibits a micro- or nanoparticle form.

In a third aspect, the present invention refers to the use of an organosilicon progressive photoprotective polymer as defined above, in the preparation of a cosmetic or dermatological composition for protecting a human or animal living body from UV radiation.

In a fourth aspect, the present invention refers to the use of a photoprotective polymer as defined above as photochemical precursor of UV absorbers.

In a fifth aspect, the present invention refers to the use of a photoprotective polymer as defined above, in the preparation of a cosmetic or dermatological composition to be applied to human or animal living body, characterized by a progressive UV protection depending on the time to sun exposition and the degree of sun radiation.

In a sixth aspect, the present invention refers to a photoprotective polymer as defined above, for its use in protecting a human or animal living body from UV radiation.

In a seventh aspect, the present invention refers to a cosmetic or dermatological composition comprising an organosilicon progressive photoprotective polymer as defined above.

In an eight aspect, the present invention refers to a monomer of formula (I):

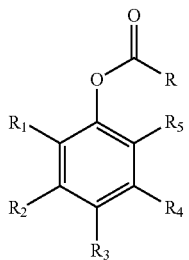
(I)

wherein:

R is selected from the group consisting of (i), (ii) and (iii):

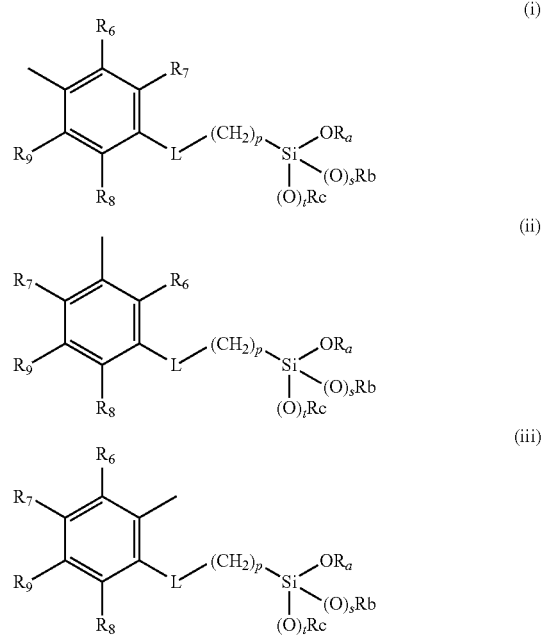

wherein:

$R_1$, $R_2$, $R_3$, $R_4$ and $R_5$ are independently selected from the group consisting of H, linear or branched $(C_1-C_6)$alkyl, $(C_3-C_6)$cycloalkyl, $OR_{10}$, $NH_2$, $NHR_{11}$, $NR_{12}R_{13}$, COOH, $COOR_{14}$, $CONH_2$, $CONHR_{15}$, $CONR_{16}R_{17}$, $SO_2NH_2$, $SO_2NHR_{18}$, and $SO_2NR_{19}R_{20}$, with the proviso that at least one of $R_1$, $R_2$, $R_3$, $R_4$ and $R_5$ is not H provided that at least one of $R_1$ and $R_5$ is H;

$R_6$, $R_7$, $R_8$ and $R_9$ are independently selected from hydrogen, linear or branched $(C_1-C_6)$alkyl, $(C_3-C_6)$cycloalkyl, $OR'_1$, $NH_2$, $NHR_2'$ and $NR_3'R_4'$;

$R_{10}$ is linear or branched $(C_1-C_6)$alkyl or $(C_3-C_6)$cycloalkyl;

$R_{11}$ is linear or branched $(C_1-C_6)$alkyl or $(C_3-C_6)$cycloalkyl;

$R_{12}$ is linear or branched $(C_1-C_6)$alkyl or $(C_3-C_6)$cycloalkyl;

$R_{13}$ is linear or branched $(C_1-C_6)$alkyl or $(C_3-C_6)$cycloalkyl; or $R_{12}$ and $R_{13}$ taken together with the nitrogen atom to which they are attached form a pyrrolidine, piperidine or morpholine ring;

$R_{14}$ is linear or branched $(C_1-C_6)$alkyl or $(C_3-C_6)$cycloalkyl;

$R_{15}$ is linear or branched $(C_1-C_6)$alkyl or $(C_3-C_6)$cycloalkyl;

$R_{16}$ is linear or branched $(C_1-C_6)$alkyl or $(C_3-C_6)$cycloalkyl;

$R_{17}$ is linear or branched $(C_1-C_6)$alkyl or $(C_3-C_6)$cycloalkyl; or $R_{16}$ and $R_{17}$ taken together with the nitrogen atom to which they are attached form a pyrrolidine, piperidine or morpholine ring;

$R_{18}$ is linear or branched $(C_1-C_6)$alkyl or $(C_3-C_6)$cycloalkyl;

$R_{19}$ is linear or branched $(C_1-C_6)$alkyl or $(C_3-C_6)$cycloalkyl;

$R_{20}$ is linear or branched $(C_1-C_6)$alkyl or $(C_3-C_6)$cycloalkyl; or $R_{19}$ and $R_{20}$ taken together with the nitrogen atom to which they are attached form a pyrrolidine, piperidine or morpholine ring;
L is a linker selected from:
—CH=N—
—(CH$_2$)—O—C(O)—NH—
$R_a$ is linear or branched (C$_1$-C$_6$)alkyl, linear or branched (C$_2$-C$_6$)alkenyl, (C$_3$-C$_6$)cycloalkyl or phenyl;
$R_b$ is linear or branched (C$_1$-C$_6$)alkyl, linear or branched (C$_2$-C$_6$)alkenyl, (C$_3$-C$_6$)cycloalkyl or phenyl;
$R_c$ is linear or branched (C$_1$-C$_6$)alkyl, linear or branched (C$_2$-C$_6$)alkenyl, (C$_3$-C$_6$)cycloalkyl or phenyl;
$R'_1$ is linear or branched (C$_1$-C$_6$)alkyl or (C$_3$-C$_6$)cycloalkyl;
$R'_2$ is linear or branched (C$_1$-C$_6$)alkyl or (C$_3$-C$_6$)cycloalkyl;
$R'_3$ is linear or branched (C$_1$-C$_6$)alkyl or (C$_3$-C$_6$)cycloalkyl;
$R'_4$ is linear or branched (C$_1$-C$_6$)alkyl or (C$_3$-C$_6$)cycloalkyl; or $R'_3$ and $R'_4$ taken together with the nitrogen atom to which they are attached form a pyrrolidine, piperidine or morpholine ring;
p is an integer selected from 2, 3 and 4;
s is an integer selected from 0 and 1;
t is an integer selected from 0 and 1;
or enantiomeric forms, or cosmetically or dermatologically acceptable salts thereof.

In a ninth aspect, the present invention relates to a process for the preparation of a monomer of formula (I) as defined above when L is a group —CH=N—, which comprises the reaction of a compound of formula (II):

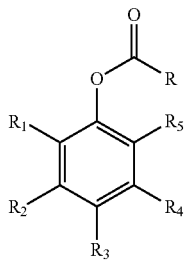
(II)

wherein:
$R_1$, $R_2$, $R_3$, $R_4$ and $R_5$ are independently selected from the group consisting of H, linear or branched (C$_1$-C$_6$)alkyl, (C$_3$-C$_6$)cycloalkyl, OR$_{10}$, NH$_2$, NHR$_{11}$, NR$_{12}$R$_{13}$, COOH, COOR$_{14}$, CONH$_2$, CONHR$_{15}$, CONR$_{16}$R$_{17}$, SO$_2$NH$_2$, SO$_2$NHR$_{18}$, and SO$_2$NR$_{19}$R$_{20}$, with the proviso that at least one of $R_1$, $R_2$, $R_3$, $R_4$ and $R_5$ is not H provided that at least one of $R_1$ and $R_5$ is H;
$R_{10}$ is linear or branched (C$_1$-C$_6$)alkyl or (C$_3$-C$_6$)cycloalkyl;
$R_{11}$ is linear or branched (C$_1$-C$_6$)alkyl or (C$_3$-C$_6$)cycloalkyl;
$R_{12}$ is linear or branched (C$_1$-C$_6$)alkyl or (C$_3$-C$_6$)cycloalkyl;
$R_{13}$ is linear or branched (C$_1$-C$_6$)alkyl or (C$_3$-C$_6$)cycloalkyl; or $R_{12}$ and $R_{13}$ taken together with the nitrogen atom to which they are attached form a pyrrolidine, piperidine or morpholine ring;
$R_{14}$ is linear or branched (C$_1$-C$_6$)alkyl or (C$_3$-C$_6$)cycloalkyl;
$R_{15}$ is linear or branched (C$_1$-C$_6$)alkyl or (C$_3$-C$_6$)cycloalkyl;
$R_{16}$ is linear or branched (C$_1$-C$_6$)alkyl or (C$_3$-C$_6$)cycloalkyl;
$R_{17}$ is linear or branched (C$_1$-C$_6$)alkyl or (C$_3$-C$_6$)cycloalkyl; or $R_{16}$ and $R_{17}$ taken together with the nitrogen atom to which they are attached form a pyrrolidine, piperidine or morpholine ring;
$R_{18}$ is linear or branched (C$_1$-C$_6$)alkyl or (C$_3$-C$_6$)cycloalkyl;
$R_{19}$ is linear or branched (C$_1$-C$_6$)alkyl or (C$_3$-C$_6$)cycloalkyl;
$R_{20}$ is linear or branched (C$_1$-C$_6$)alkyl or (C$_3$-C$_6$)cycloalkyl; or $R_{19}$ and $R_{20}$ taken together with the nitrogen atom to which they are attached form a pyrrolidine, piperidine or morpholine ring; and
R' is selected from (i'), (ii') and (iii'):

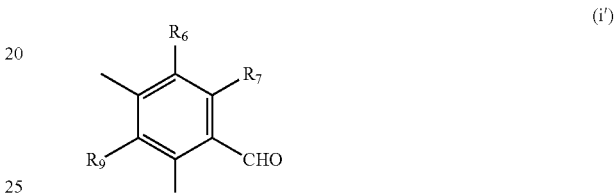
(i')

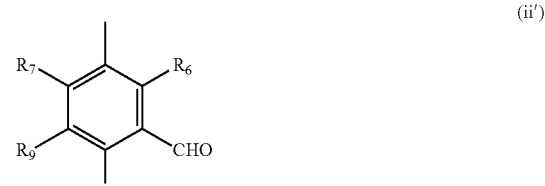
(ii')

(iii')

wherein:
$R_6$, $R_7$, $R_8$ and $R_9$ are independently selected from hydrogen, linear or branched (C$_1$-C$_6$)alkyl, (C$_3$-C$_6$)cycloalkyl, OR'$_1$, NH$_2$, NHR$_2$' and NR$_3$'R$_4$';
with a compound of formula (III):

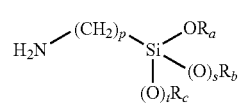
(III)

wherein:
$R_a$ is linear or branched (C$_1$-C$_6$)alkyl, linear or branched (C$_2$-C$_6$)alkenyl, (C$_3$-C$_6$)cycloalkyl or phenyl;
$R_b$ is linear or branched (C$_1$-C$_6$)alkyl, linear or branched (C$_2$-C$_6$)alkenyl, (C$_3$-C$_6$)cycloalkyl or phenyl;
$R_c$ is linear or branched (C$_1$-C$_6$)alkyl, linear or branched (C$_2$-C$_6$)alkenyl, (C$_3$-C$_6$)cycloalkyl or phenyl;
p is an integer selected from 2, 3 and 4;
s is an integer selected from 0 and 1;
t is an integer selected from 0 and 1.

In an tenth aspect, the present invention relates to a process for the preparation of a monomer of formula (I) as defined above, when L is —CH₂—O—C(O)—NH—, which comprises:

a) the reduction reaction of a compound of formula (II) as defined above, in the presence of a reducing agent, to produce a compound of formula (V):

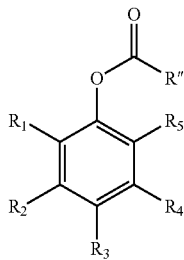

(V)

wherein:
R₁-R₅ are as defined above; and
R″ is selected from (I″), (ii″) and (iii″):

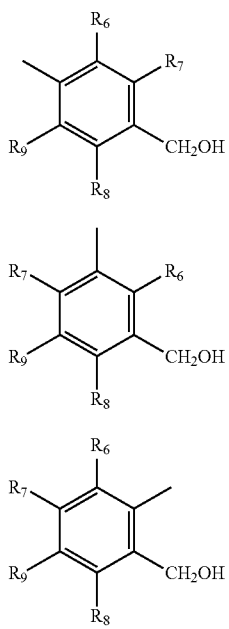

and b) the reaction of the compound of formula (V) as defined above with a compound of formula (VI):

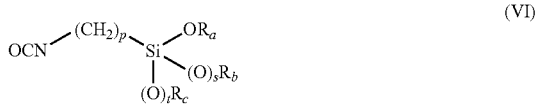

(VI)

wherein:
Rₐ is linear or branched (C₁-C₆)alkyl, linear or branched (C₂-C₆)alkenyl, (C₃-C₆)cycloalkyl or phenyl;

R_b is linear or branched (C₁-C₆)alkyl, linear or branched (C₂-C₆)alkenyl, (C₃-C₆)cycloalkyl or phenyl;
R_c is linear or branched (C₁-C₆)alkyl, linear or branched (C₂-C₆)alkenyl, (C₃-C₆)cycloalkyl or phenyl;
p is an integer selected from 2, 3 and 4;
s is an integer selected from 0 and 1;
t is an integer selected from 0 and 1.

Figure 1:
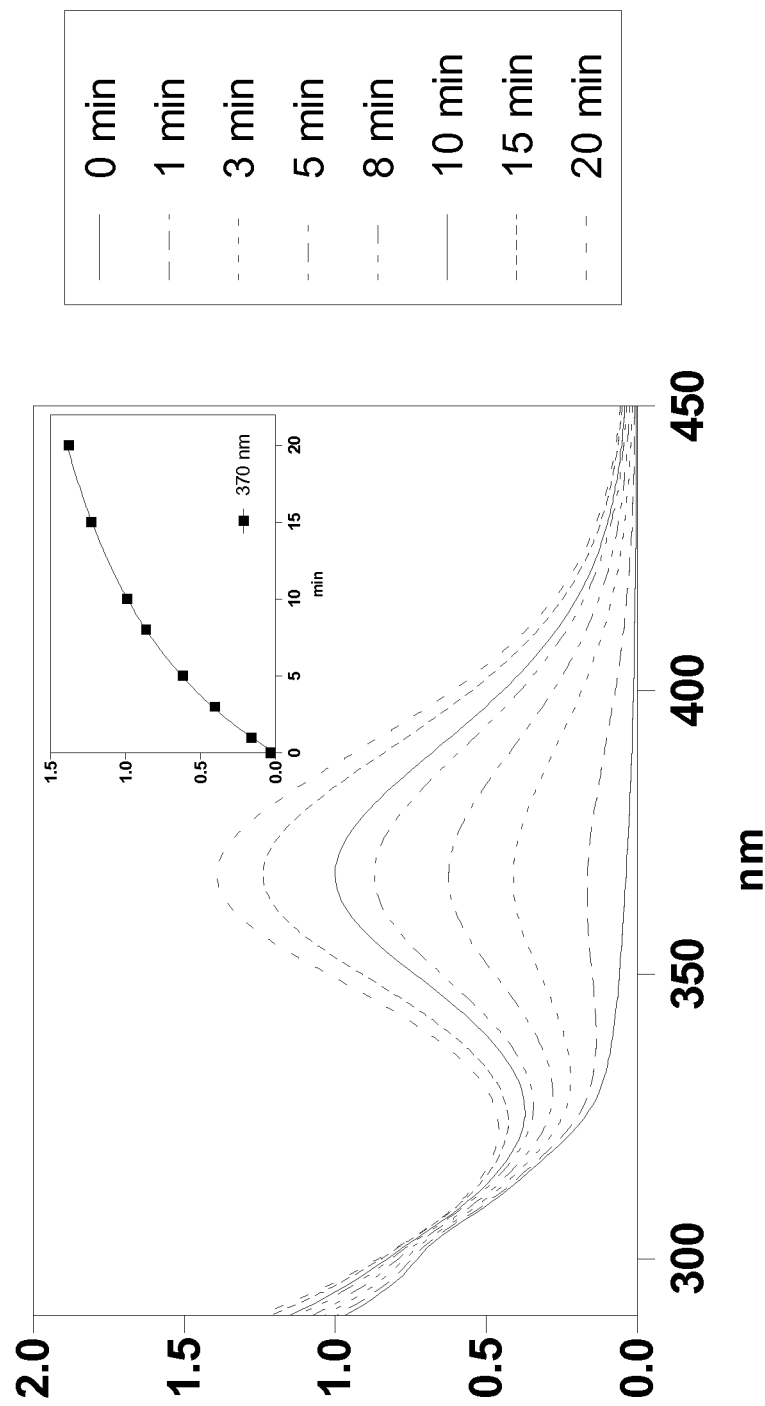
FIG. 1 shows the UV-Vis spectrum of 3-(diethylamino) phenyl 4-((3-(triethoxysilyl)propylimino)methyl)benzoate particles.
Figure 2:
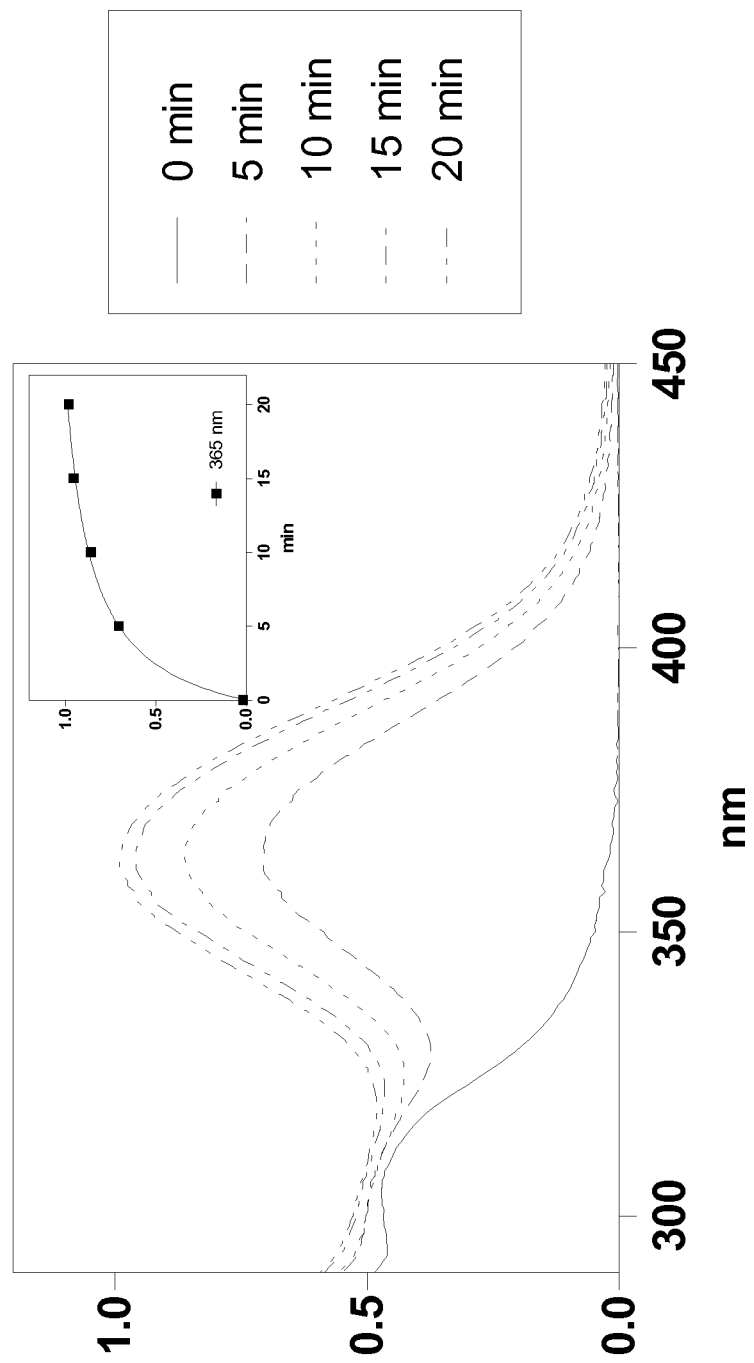
FIG. 2 shows the UV-Vis spectrum of 3-(diethylamino) phenyl 4-((3-(triethoxysilyl)propylcarbamoyloxy)methyl) benzoate particles.
Figure 3:
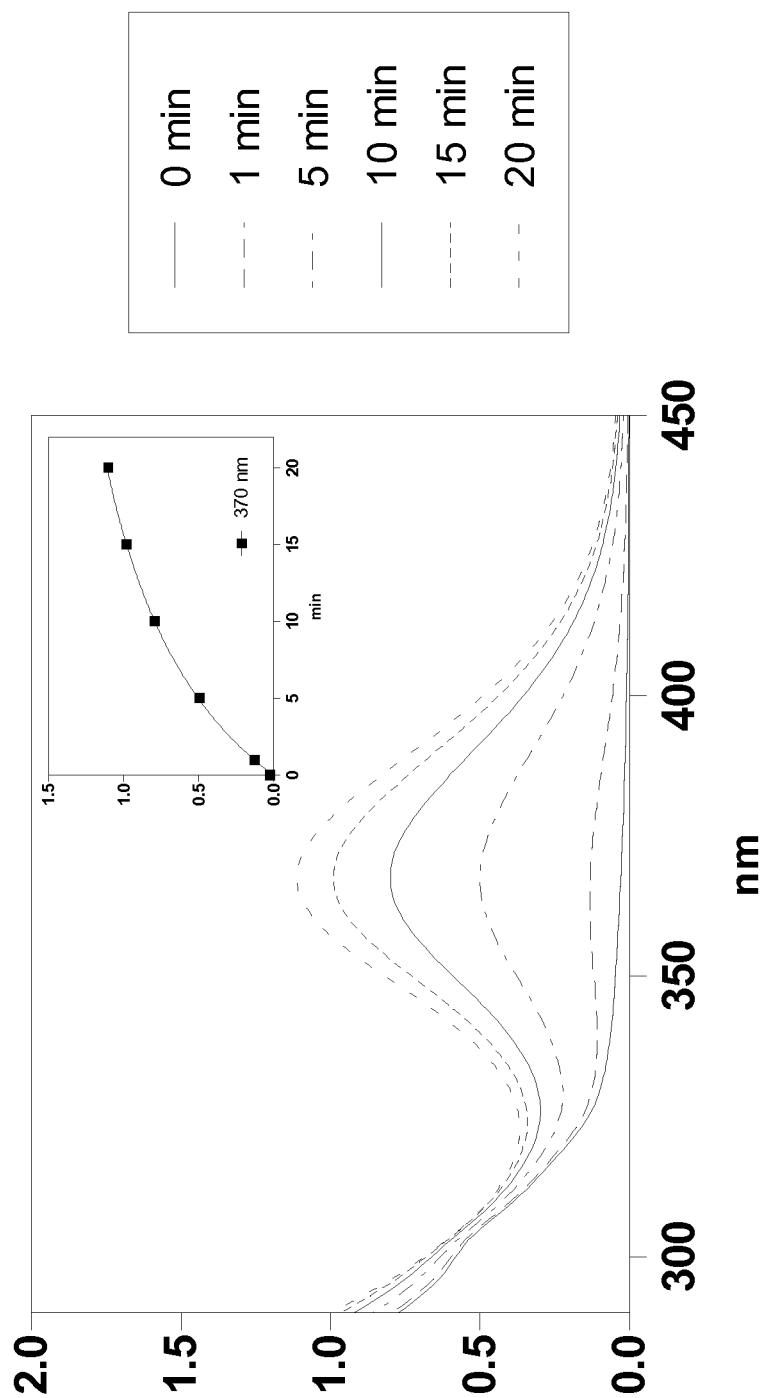
FIG. 3 shows the UV-Vis spectrum of 3-(dimethylamino) phenyl 4-((3-(triethoxysilyl)propylcarbamoyloxy)methyl) benzoate particles.
Figure 4:
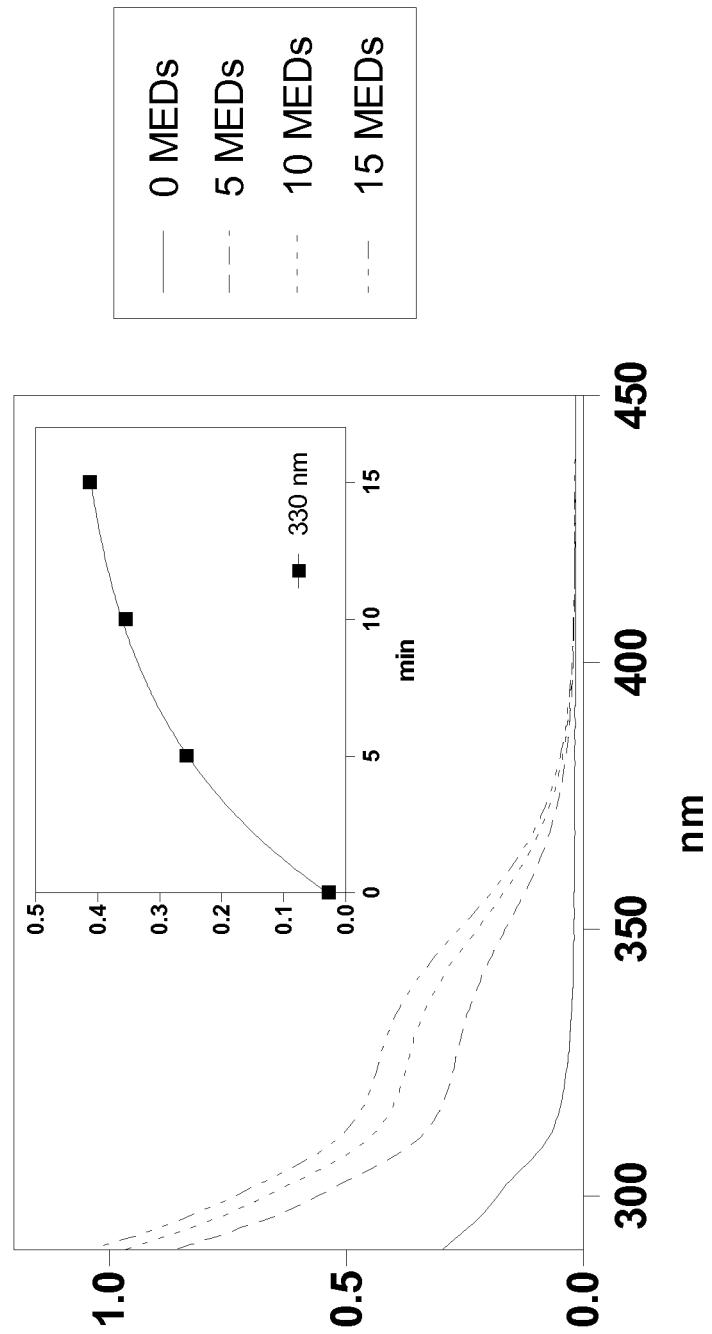
FIG. 4 shows the UV-Vis spectrum of 3-methoxyphenyl 4-((3-(triethoxysilyl)propylcarbamoyloxy)methyl)benzoate particles.
Figure 5:
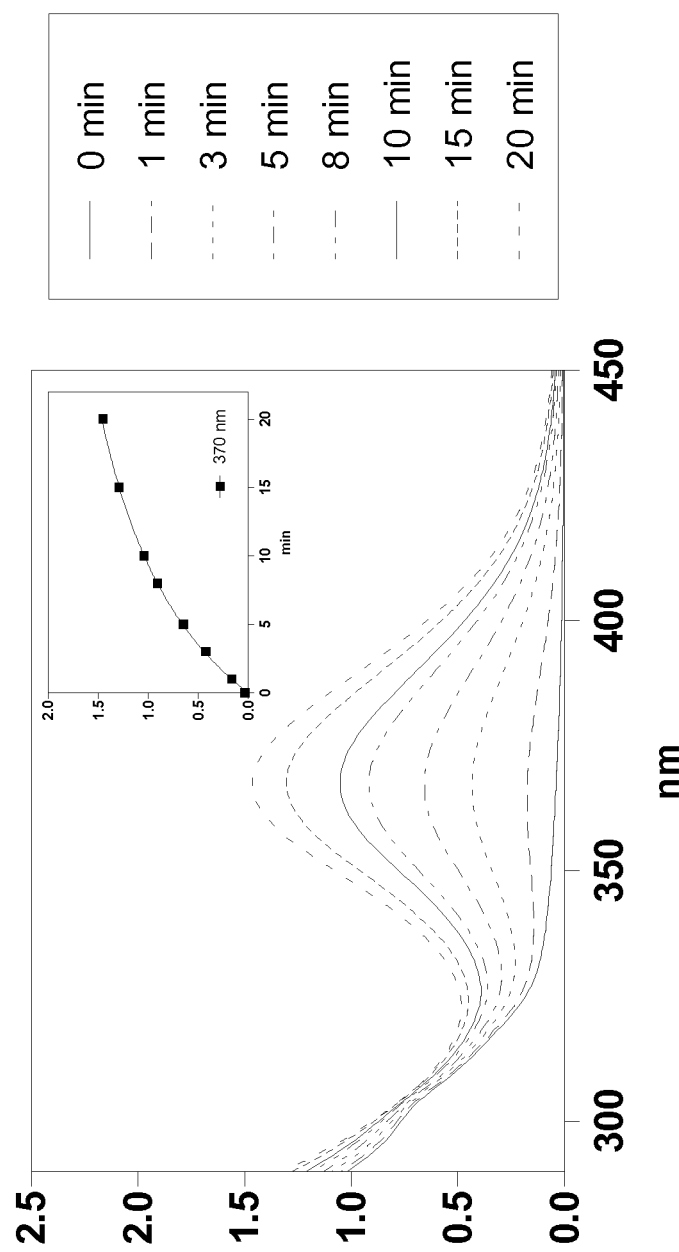
FIG. 5 shows the UV-Vis spectrum of 3-(dimethylamino) phenyl 4-((3-(triethoxysilyl)propylimino)methyl)benzoate particles.
Figure 6:
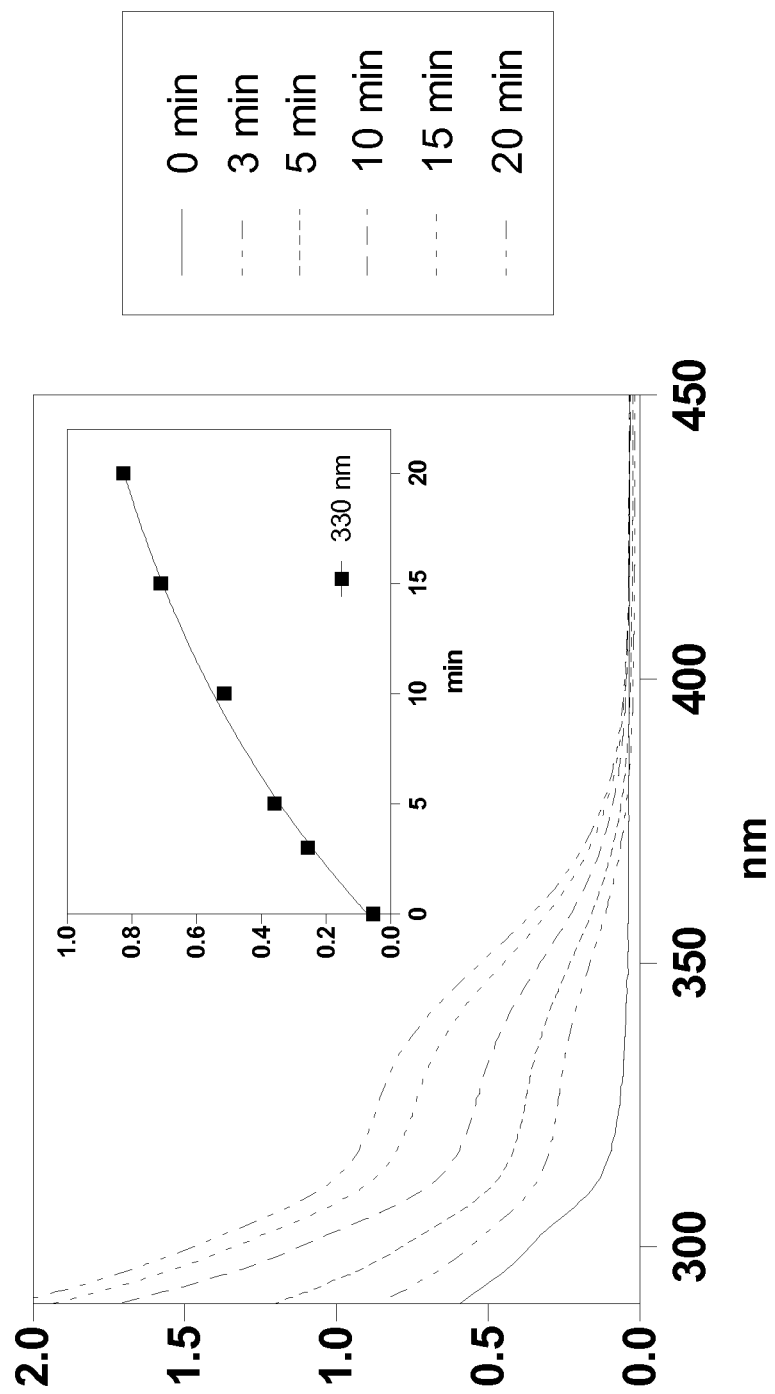
FIG. 6 shows the UV-Vis spectrum of 3-methoxyphenyl 4-((3-(triethoxysilyl)propylimino)methyl)benzoate particles.

In all figures the axis of ordinates represents absorbance or extinction 1%, and the axis of abscises represents wavelength in nm. Small drawings in the figures depict absorbance kinetics measurements at a selected wavelength, as indicated.

DETAILED DESCRIPTION OF THE INVENTION

In the context of the present invention, the following terms have the meaning detailed below.

"$C_1$-$C_6$ alkyl" refers to a linear or branched hydrocarbon chain radical consisting of 1 to 6 carbons, containing no unsaturation, and which is attached to the rest of the molecule by a single bond, e.g., methyl, ethyl, 1-propyl, 2-propyl, 1-butyl, t-butyl, 1-pentyl, etc. Alkyl radicals may be optionally substituted by one or more substituents such as aryl, halo, hydroxy, alkoxy, carboxy, cyano, carbonyl, acyl, amino, nitro, mercapto, alkylthio, etc, provided that they do not affect the polymerization process.

"$C_2$-$C_6$ alkenyl" refers to an alkyl radical as defined above consisting of 2 to 6 carbons and having one or more unsaturated bonds.

"$C_3$-$C_6$ cycloalkyl" refers to a stable 3-to 6-membered monocyclic radical which is saturated or partially saturated, and which consist solely of carbon and hydrogen atoms, such as cyclohexyl or adamantyl. Cycloalkyl radicals may be optionally substituted by one or more substituents such as alkyl, halo, hydroxy, amino, cyano, nitro, alkoxy, carboxy, etc, provided that they do not affect the polymerization process.

The term "alkanol" refers to a linear or branched hydrocarbon chain radical having 1 to 6 carbon atoms and containing a hydroxyl group.

The term "cosmetically or dermatologically acceptable salts" in the context of this invention must be understood as any salt that is tolerated physiologically (normally meaning that it is not toxic, particularly, as a result of the counter-ion) when applied or used, particularly, in humans and/or mammals. Examples of these salts include acid addition salts and alkali addition salts. Acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

In a first aspect, the present invention refers to a process (from now onwards process 1) for the preparation of an organosilicon progressive photoprotective polymer, which comprises the reaction of a monomer of formula (I) as defined above with a compound of formula (IV) as defined above in an alkanol/water mixture.

In a preferred embodiment, in the monomer of formula (I) used in the process 1 of the invention $R_1$, $R_3$, $R_4$ and $R_5$ are H.

In another preferred embodiment, $R_2$ is selected from $OR_{10}$, $NH_2$, $NHR_{11}$ and $NR_{12}R_{13}$, wherein $R_{10}$, $R_{11}$, $R_{12}$ and $R_{13}$ are a linear ($C_1$-$C_6$) alkyl group. Even more preferably, $R_2$ is selected from $OR_{10}$ and $NR_{12}R_{13}$, wherein $R_{10}$, $R_{12}$ and $R_{13}$ are also a linear ($C_1$-$C_6$) alkyl group, more preferably a methyl or ethyl group.

Even more preferably, in the monomer of formula (I) used in the process (1), $R_1$, $R_3$, $R_4$ and $R_5$ are H, and $R_2$ is selected from $OR_{10}$, $NH_2$, $NHR_{11}$ and $NR_{12}R_{13}$, wherein $R_{10}$, $R_{11}$, $R_{12}$ and $R_{13}$ are a linear ($C_1$-$C_6$) alkyl group. Even more preferably, $R_2$ is selected from $OR_{10}$ and $NR_{12}R_{13}$, wherein $R_{10}$, $R_{12}$ and $R_{13}$ are also a linear ($C_1$-$C_6$) alkyl group, more preferably a methyl or ethyl group.

In another preferred embodiment, $R_6$-$R_9$ are all H.

In an additional preferred embodiment, p is 3.

In another preferred embodiment, s and t are both 1.

In another preferred embodiment, $R_a$, $R_b$ and $R_c$ are a linear ($C_1$-$C_6$) alkyl group, more preferably an ethyl group.

Even in another preferred embodiment, R is (i).

In another preferred embodiment, in the monomer of formula (I) used in the process 1 of the invention $R_1$, $R_3$-$R_5$ are H; $R_6$-$R_9$ are H; $R_2$ is selected from $OR_{10}$, $NH_2$, $NHR_{11}$ and $NR_{12}R_{13}$, more preferably from $OR_{10}$ and $NR_{12}R_{13}$, wherein $R_{10}$, $R_{11}$, $R_{12}$ and $R_{13}$ are a linear ($C_1$-$C_6$) alkyl group, more preferably a methyl or ethyl group; p is 3; s and t are 1; and $R_a$, $R_b$ and $R_c$ are a linear ($C_1$-$C_6$) alkyl group. In a particular embodiment of this preferred embodiment, R is (i). It has been observed that these compounds provide the best conversion efficiencies and, therefore, an improved level of photoprotection.

In another preferred embodiment, the monomer of formula (I) used in the process 1 of the invention is selected from the group consisting of:
  3-(diethylamino)phenyl 4-((3-(triethoxysilyl)propyl carbamoyloxy)methyl)benzoate
  3-(dimethylamino)phenyl 4-((3-(triethoxysilyl)propyl carbamoyloxy)methyl)benzoate
  3-methoxyphenyl 4-((3-(triethoxysilyl)propylcarbamoyloxy)methyl)benzoate
  3-(diethylamino)phenyl 4-((3-(triethoxysilyl)propylimino)methyl)benzoate
  3-(dimethylamino)phenyl 4-((3-(triethoxysilyl)propylimino)methyl)benzoate
  3-methoxyphenyl 4-((3-(triethoxysilyl)propylimino) methyl) benzoate.

In a particular embodiment, in the silane of formula (IV) used in the process 1 of the invention, $R_d$, $R_e$, $R_f$ and $R_g$ are independently a linear or branched ($C_1$-$C_6$) alkyl, more preferably all of them are a linear ($C_1$-$C_6$) alkyl, even more preferably they are an ethyl group.

In another preferred embodiment, in the silane of formula (IV) used in the process 1 of the invention, $w_1$ and $w_2$ are both 1.

Even more preferably, the silane of formula (IV) is tetraethoxysilane (TEOS).

In a particular embodiment of the invention, process 1 is carried out in the presence of a nitrogen-containing basic compound selected from the group consisting of ammonia, mono-alkylamine, di-alkylamine, tri-alkylamine, mono-alkanolamine, di-alkanolamine and tri-alkanolamine. Both alkyl and alkanol groups are linear or branched, having 1 to 6 carbon atoms. Preferably, the nitrogen-containing basic compound is ammonia.

In a second aspect, the present invention relates to an organosilicon progressive photoprotective polymer obtainable by process 1 of the invention.

The photoprotective polymers of the present invention obtainable as shown in this specification exhibit a micro- or nanoparticle form. Moreover, such particles have homogenous and spherical or quasi spherical form and are essentially hermetic.

In the context of the present invention, by the term "micro- or nano-particle form" it is understood particles having an average size lower than 100 microns. Usually, said particles have an average size ranging from 10 nm to 10 microns, preferably form 100 to 1500 nm.

The preparation of the particles by the process 1 of the invention has the advantage that the product can be obtained in the form of a suspension containing about 1 to 25% solids consisting of the hermetic spherical or quasi spherical particles which can directly be used in cosmetic or dermatological compositions of the present invention. As mentioned before, the hermetism is a relevant physical property of the polymers of the invention since the release of benzoic acid esters or their phototransformation products is minimised.

The photoprotective activity is due to in situ conversion to sunscreen 2-hydroxybenzophenone polymers through a photo-Fries rearrangement of the benzoic acid ester fragment to a 2-hydroxybenzophenone fragment as shown in Scheme 1 for illustrative purposes:

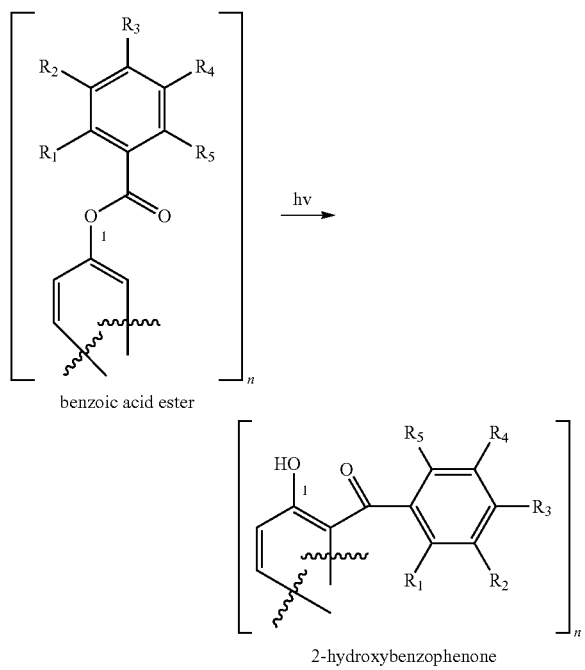

benzoic acid ester 2-hydroxybenzophenone wherein $R_1$-$R_5$, and n is the number of monomeric units constituting the polymer.

These photoprotective polymers show a progressive UV protection depending on the time of sun exposure and the dose of sun radiation absorbed by the polymer. This progressive UV protection property is evidenced in their UVB and UVA screening ability. The extent of photo-Fries rearrangement is indicative of the amount of UVB radiation received.

Consequently, the compositions containing these photoprotective polymers provide a safer method to take sunbaths than conventional sunscreen products, since protection increases with time of sun exposure and dose of radiation.

Therefore, in another aspect the present invention relates to the use of a photoprotective polymer as defined above in the preparation of a cosmetic or dermatological composition for protecting a human or animal living body from UV radiation.

In another aspect the present invention relates to the use of a photoprotective polymer as defined above as photochemical precursors of UV absorbers.

In another aspect, the present invention refers to the use of a photoprotective polymer as defined above in the preparation of a cosmetic or dermatological composition to be applied to human or animal living body, characterized by a progressive UV protection depending on the time to sun exposition and the degree of sun radiation.

In another aspect, the present invention refers to a photoprotective polymer as defined above for it use in protecting a human or animal living body from UV radiation.

Another aspect of the invention refers to a cosmetic or dermatological composition comprising an organosilicon progressive photoprotective polymer as defined above or a mixture thereof.

The present invention also relates to a cosmetic or dermatological composition as mentioned before comprising an effective amount of a polymer as defined above, or a mixture thereof, susceptible to be photochemically converted in situ to a sunscreen compound with enhanced UV protection ability.

In a particular embodiment of the invention, the content of the photoprotective polymers in the cosmetic or dermatological composition ranges from 0.01% and 40% by weight, based on the total weight of the composition. Preferably, the amount falls within the range of 0.05 to 25% by weight, more preferably falls within 0.1 and 15% by weight.

The cosmetic or dermatologic composition of the invention may also contain at least one additional organic sunscreen compound for filtering UVB or UVA rays. In a preferred embodiment, said additional sunscreen compound is selected from avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrylate, 2-ethylhexylsalicylate, glyceryl p-aminobenzoate, 3,3,5-trimethylcyclohexylsalicylate, methylanthranylate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hidroxybenzoyl)benzoate, 2-(4-methylbenzyliden)-camphor, and 4-isopropyldibenzoylmethane.

Furthermore, the composition of the invention may additionally contain usual adjuvants and additives such as preservatives, antioxidants, fatty substances, oil, water, organic solvents, silicones, thickeners, softeners, emulsifiers, antifoaming agents, moisturizers, fragrances, surfactants, fillers, sequestering agents, anionic, cationic, nonionic or amphoteric polymers or mixtures thereof, propellants acidifying or basifying agents, dyes, colorants, pigments, nanopigments, or any other ingredient usually formulated into cosmetics, in particular those for the production of sunscreen compositions.

The necessary amounts of the cosmetic and dermatological adjuvants and additives can, based on the desired product, easily be chosen by a skilled artisan in this field and will be illustrated in the examples, without being limited hereto. In a preferred embodiment of the invention, the content of the adjuvants and/or additives in the cosmetic or dermatological composition ranges from 0.01% and 40% by weight, based on the total weight of the composition. Preferably, this amount falls within the range of 0.05 to 25% by weight, more preferably falls within 0.1 and 15% by weight.

In another particular embodiment, the cosmetic or dermatological composition of the invention comprises a polymer according to the second aspect of the invention or a mixture thereof, characterized in that the content of polymers ranges from 0.01% to 40% by weight, based on the total weight of the composition, preferably from 0.05% to 25%, and more preferably from 0.01% to 15%, and a sunscreen compound, which is selected from avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrilate, 2-ethylhexylsalicilate, glyceryl p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hidroxybenzoyl)benzoate, 2-(4-methylbenzyliden)-camphor, and 4-isopropyldibenzoylmethane, the content of sunscreen compound ranging from 0.01% to 40% by weight, based on the total weight of the composition, preferably from 0.05% to 25%, and more preferably from 0.01% to 15% to be applied to human or animal living body.

The cosmetic or dermatological composition of the invention can, in particular, be provided in the form of creams, ointments, milks, suspensions, powders, oils, lotions, gels, sticks, foams, emulsions, dispersions, sprays, aerosols, lipsticks, foundations, make-up, loose or press powders, eye blushes, eye shadows, mascaras, nail varnishes, nail lacquers, and non permanent dyeing compositions for the hair.

In another aspect, the present invention refers to a monomer of formula (I) according to the eighth aspect of the invention.

In a preferred embodiment, $R_1$, $R_3$, $R_4$ and $R_5$ are H.

In another preferred embodiment, $R_2$ is selected from $OR_{10}$, $NH_2$, $NHR_{11}$ and $NR_{12}R_{13}$, wherein $R_{10}$, $R_{11}$, $R_{12}$ and $R_{13}$ are a linear ($C_1$-$C_6$) alkyl group. Even more preferably, $R_2$ is selected from $OR_{10}$ and $NR_{12}R_{13}$, wherein $R_{10}$, $R_{12}$ and $R_{13}$ are also a linear ($C_1$-$C_6$) alkyl group, more preferably a methyl or ethyl group.

In another preferred embodiment, $R_6$-$R_9$ are all H.

In an additional preferred embodiment, p is 3.

In another preferred embodiment, s and t are both 1.

In another preferred embodiment, $R_a$, $R_b$ and $R_c$ are a linear ($C_1$-$C_6$) alkyl group, more preferably an ethyl group.

Even in another preferred embodiment, R is (i).

In another preferred embodiment, $R_1$, $R_3$-$R_5$ are H; $R_6$-$R_9$ are H; $R_2$ is selected from $OR_{10}$, $NH_2$, $NHR_{11}$ and $NR_{12}R_{13}$, more preferably from $OR_{10}$ and $NR_{12}R_{13}$, wherein $R_{10}$, $R_{11}$, $R_{12}$ and $R_{13}$ are a linear ($C_1$-$C_6$) alkyl group, more preferably a methyl or ethyl group; p is 3; s and t are 1; and $R_a$, $R_b$ and $R_c$ are a linear ($C_1$-$C_6$) alkyl group. In a particular embodiment of this preferred embodiment, R is (i).

In another preferred embodiment, the monomer of formula (I) is selected from the group consisting of:
  3-(diethylamino)phenyl 4-((3-(triethoxysilyl)propyl carbamoyloxy)methyl)benzoate
  3-(dimethylamino)phenyl 4-((3-(triethoxysilyl)propyl carbamoyloxy)methyl)benzoate
  3-methoxyphenyl 4-((3-(triethoxysilyl)propylcarbamoyloxy) methyl)benzoate
  3-(diethylamino)phenyl 4-((3-(triethoxysilyl)propylimino)methyl)benzoate
  3-(dimethylamino)phenyl 4-((3-(triethoxysilyl)propylimino)methyl)benzoate
  3-methoxyphenyl 4-((3-(triethoxysilyl)propylimino) methyl) benzoate.

In another aspect, the present invention refers to a process for the preparation of a monomer of formula (I) as defined above when linker L is a group —CH=N—, which comprises the reaction of a compound of formula (II) with a compound of formula (III) according to the ninth aspect of the invention.

This reaction between the aldehyde group of the compound of formula (II) and the amine group of the compound of formula (III) provides the imine group (—CH=N—) as well as a stoichiometric amount of water. In order to eliminate the water and to prevent the reversal of the reaction, any method known to those skilled in the art to remove water can be used. In a particular embodiment, this reaction takes place in the presence of a water removal agent, such as, for example anhydrous magnesium sulphate.

The present invention also relates to a process for the preparation of a monomer of formula (I) as defined above, when linker L is a group —($CH_2$)—O—C(O)—NH—, which comprises the reduction reaction of a compound of formula (II) to produce a compound of formula (V) in the presence of a reducing agent, and the reaction of the compound of formula (V) with a compound of formula (VI) according to the tenth aspect of the invention.

Any reducing agent known by a skilled person for this type of reactions can be used in the synthesis of the monomer of formula (I). In a particular embodiment, the reducing agent is sodium borohydride.

Compounds of formula (II) and (III) are prepared from commercially available starting reactants by conventional known methods of organic chemistry as described in the examples provided in the present specification. For example, the compound of formula (II) can be obtained according to the following scheme reaction [substituents $R_1$-$R_9$ not shown]:

Cosmetically or dermatologically acceptable salts of the monomers of formula (I) are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred.

The following examples are provided to further illustrate certain embodiments of the invention and cannot be considered as restricting the scope of the invention in any way.

EXAMPLES

Example 1. Synthesis of 3-(diethylamino)phenyl 4-((3-(triethoxysilyl)propyl carbamoyloxy)methyl) benzoate (Compound 1)

Step 1: Synthesis of 4-formylbenzoyl chloride 0.92 g (6.13 mmol) of 4-formylbenzoic acid were suspended in 50 mL of anhydrous toluene. 16 mL of thionyl chloride (0.22 mol) were added and the resulting suspension was heated at 130° C. for 3 hours under nitrogen atmosphere, then cooled to room temperature and the solvent evaporated under reduced pressure. 50 extra mL of toluene were added and evaporated under reduced pressure to eliminate possible remaining thionyl chloride. This process was repeated twice. The solid obtained was used immediately without further purification.

Step 2: Synthesis of 3-(diethylamino)phenyl 4-formylbenzoate 1.01 g (6.13 mmol) of 3-(diethylamino)phenol were suspended in 50 mL of dichloromethane and solubilized by adding 0.85 mL (6.13 mmol) of triethylamine. The resulting solution was stirred for 30 minutes and after this time a solution containing 4-formylbenzoyl chloride in dichloromethane (6.13 mmol of acyl chloride in 20 mL of solvent) was added dropwise. The resulting solution was stirred at room temperature for 5 hours, then extracted with saturated aqueous solution of sodium carbonate (3×40 mL), dried over magnesium sulfate and the solvent evaporated under reduced pressure. The brownish solid obtained was recrystallized with cyclohexane, yielding a yellowish solid (50% yield, 95% purity assessed by HPLC).

$^1$H-NMR (CDCl$_3$): 10.15 ppm (s, 1H), 8.37 ppm (d, 2H), 8.02 ppm (d, 2H), 7.24 ppm (t, 1H), 6.57 ppm (dd, 1H), 6.47 ppm (m, 2H), 3.35 ppm (q, 4H), 1.23 ppm (t, 6H)

Step 3: Synthesis of 3-(diethylamino)phenyl 4-(hydroxymethyl)benzoate 2.00 g (6.72 mmol) of 3-(diethylamino)phenyl 4-formylbenzoate were suspended in 50 mL of anhydrous ethanol and 0.80 g (3 eq) of sodium borohydride were added in small portions in an ice bath. After complete addition, the solution was stirred at room temperature for 30 minutes. Then, 30 mL of water were added and the stirring was continued for half an hour. Chloroform (3×50 mL) was added and the organic phase was extracted, dried over magnesium sulfate and the solvent evaporated under reduced pressure to yield the desired product as a yellow solid (90% yield).

$^1$H-NMR (CDCl$_3$): 8.20 ppm (d, 2H), 7.49 ppm (d, 2H), 7.24 ppm (t, 1H), 6.57 ppm (dd, 1H), 6.47 ppm (m, 2H), 4.80 ppm (s, 2H), 3.35 ppm (q, 4H), 1.23 ppm (t, 6H)

Step 4: Synthesis of 3-(diethylamino)phenyl 4-((3-(triethoxysilyl)propylcarbamoyloxy)methyl)benzoate 1.15 g (3.84 mmol) of 3-(diethylamino)phenyl 4-(hydroxymethyl)benzoate were dissolved in 100 mL of chloroform and 2.85 mL (3 eq) of 3-(triethoxysilyl)propyl isocyanate and 1.60 mL (3 eq) of triethylamine were added. The resulting solution was refluxed for 48 hours. Once cooled to room temperature again, the solvent was evaporated under reduced pressure and the excess of reactants were distilled at vacuum, yielding the desired product as an oil (quantitative yield).

$^1$H-NMR (CDCl$_3$): 8.20 ppm (d, 2H), 7.49 ppm (d, 2H), 7.24 ppm (t, 1H), 6.57 ppm (dd, 1H), 6.47 ppm (m, 2H), 5.19 ppm (s, 1H), 4.80 ppm (s, 2H), 3.85 ppm (q, 6H), 3.35 ppm (q, 4H), 3.20 ppm (t, 2H), 1.61 ppm (m, 2H), 1.23 ppm (t, 9H), 1.18 ppm (t, 6H), 0.69 ppm (m, 2H).

Example 2. Synthesis of 3-(dimethylamino)phenyl 4-((3-(triethoxysilyl)propyl carbamoyloxy)methyl) benzoate (Compound 2)

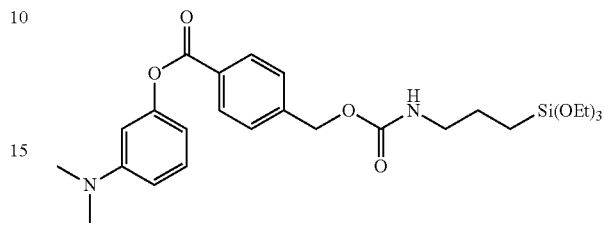

Step 1: Synthesis of 4-formylbenzoyl chloride 0.92 g (6.13 mmol) of 4-formylbenzoic acid were suspended in 50 mL of anhydrous toluene. 16 mL of thionyl chloride (0.22 mol) were added and the resulting suspension was heated at 130° C. for 3 hours under nitrogen atmosphere, then cooled to room temperature and the solvent evaporated under reduced pressure. 50 extra mL of toluene were added and evaporated under reduced pressure to eliminate possible remaining thionyl chloride. This process was repeated twice. The solid obtained was used immediately without further purification.

Step 2: Synthesis of 3-(dimethylamino)phenyl 4-formylbenzoate 0.84 g (6.13 mmol) of 3-(dimethylamino)phenol were suspended in 50 mL of dichloromethane and solubilized by adding 0.85 mL (6.13 mmol) of triethylamine. The resulting solution was stirred for 30 minutes and after this time a solution containing 4-formylbenzoyl chloride in dichloromethane (6.13 mmol of acyl chloride in 20 mL of solvent) was added dropwise. The resulting solution was stirred at room temperature for 5 hours, then extracted with saturated aqueous solution of sodium carbonate (3×40 mL), dried over magnesium sulfate and the solvent evaporated under reduced pressure. The brownish solid obtained was recrystallized with cyclohexane, yielding a yellowish solid (60% yield, 95% purity assessed by HPLC).

$^1$H-NMR (CDCl$_3$): 10.14 ppm (s, 1H), 8.37 ppm (d, 2H), 8.02 ppm (d, 2H), 7.26 ppm (t, 1H), 6.64 ppm (dd, 1H), 6.54 ppm (dd+t, 2H), 2.97 ppm (s, 6H)

Step 3: Synthesis of 3-(dimethylamino)phenyl 4-(hydroxymethyl)benzoate 2.00 g (7.43 mmol) of 3-(dimethylamino)phenyl 4-formylbenzoate were suspended in 50 mL of anhydrous ethanol and 0.80 g (3 eq) of sodium borohydride were added in small portions in an ice bath. After complete addition, the solution was stirred at room temperature for 30 minutes. Then, 30 mL of water were added and the stirring was continued for half an hour. Chloroform (3×50 mL) was added and the organic phase was extracted, dried over magnesium sulfate and the solvent evaporated under reduced pressure to yield the desired product as a yellow solid (90% yield).

¹H-NMR (CDCl₃): 8.20 ppm (d, 2H), 7.49 ppm (d, 2H), 7.26 ppm (t, 1H), 6.64 ppm (dd, 1H), 6.54 ppm (dd+t, 2H), 4.80 ppm (s, 2H), 2.97 ppm (s, 6H)

Step 4: Synthesis of 3-(dimethylamino)phenyl 4-((3-(triethoxysilyl)propylcarbamoyloxy)methyl)benzoate 1.03 g (3.84 mmol) of 3-(dimethylamino)phenyl 4-(hydroxymethyl)benzoate were dissolved in 100 mL of chloroform and 2.85 mL (3 eq) of 3-(triethoxysilyl)propyl isocyanate and 1.60 mL (3 eq) of triethylamine were added. The resulting solution was refluxed for 48 hours. Once cooled to room temperature again, the solvent was evaporated under reduced pressure and the excess of reactants were distilled at vacuum, yielding the desired product as an oil (quantitative yield).

¹H-NMR (CDCl₃): 8.20 ppm (d, 2H), 7.49 ppm (d, 2H), 7.26 ppm (t, 1H), 6.64 ppm (dd, 1H), 6.54 ppm (dd+t, 2H), 4.80 ppm (s, 2H), 3.20 ppm (t, 2H), 2.97 ppm (s, 6H), 1.61 ppm (m, 2H), 1.23 ppm (t, 9H), 0.69 ppm (m, 2H)

Example 3. Synthesis of 3-methoxyphenyl 4-((3-(triethoxysilyl)propylcarbamoyloxy)methyl)benzoate (Compound 3)

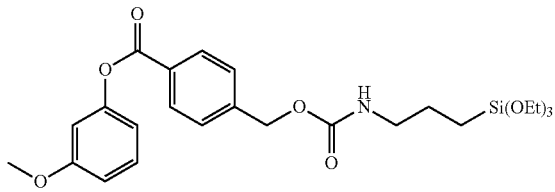

Step 1: Synthesis of 4-formylbenzoyl chloride 0.92 g (6.13 mmol) of 4-formylbenzoic acid were suspended in 50 mL of anhydrous toluene. 16 mL of thionyl chloride (0.22 mol) were added and the resulting suspension was heated at 130° C. for 3 hours under nitrogen atmosphere, then cooled to room temperature and the solvent evaporated under reduced pressure. 50 extra mL of toluene were added and evaporated under reduced pressure to eliminate possible remaining thionyl chloride. This process was repeated twice. The solid obtained was used immediately without further purification.

Step 2: Synthesis of 3-methoxyphenyl 4-formylbenzoate 0.76 g (6.13 mmol) of 3-methoxyphenol were suspended in 50 mL of dichloromethane and solubilized by adding 0.85 mL (6.13 mmol) of triethylamine. The resulting solution was stirred for 30 minutes and after this time a solution containing 4-formylbenzoyl chloride in dichloromethane (6.13 mmol of acyl chloride in 20 mL of solvent) was added dropwise. The resulting solution was stirred at room temperature for 5 hours, then extracted with saturated aqueous solution of sodium carbonate (3×40 mL), dried over magnesium sulfate and the solvent evaporated under reduced pressure. A white solid was obtained with a 96% of purity, as assessed by HPLC (90% yield).

¹H-NMR (CDCl₃): 10.14 ppm (s, 1H), 8.37 ppm (d, 2H), 8.02 ppm (d, 2H), 7.34 ppm (t, 1H), 6.84 ppm (td, 2H), 6.78 ppm (t, 1H), 3.83 ppm (s, 3H)

Step 3: Synthesis of 3-methoxy phenyl 4-(hydroxymethyl)benzoate 2.00 g (7.75 mmol) of 3-methoxyphenyl 4-formylbenzoate were suspended in 50 mL of anhydrous ethanol and 0.80 g (3 eq) of sodium borohydride were added in small portions in an ice bath. After complete addition, the solution was stirred at room temperature for 30 minutes. Then, 30 mL of water were added and the stirring was continued for half an hour. Chloroform (3×50 mL) was added and the organic phase was extracted, dried over magnesium sulfate and the solvent evaporated under reduced pressure to yield the desired product as a yellow solid (90% yield).

¹H-NMR (CDCl₃): 8.20 ppm (d, 2H), 7.50 ppm (d, 2H), 7.34 ppm (t, 1H), 6.84 ppm (td, 2H), 6.78 ppm (t, 1H), 4.8 ppm (s, 2H), 3.83 ppm (s, 3H)

Step 4: Synthesis of 3-methoxyphenyl 4-((3-(triethoxysilyl)propylcarbamoyloxy)methyl)benzoate 0.99 g (3.84 mmol) of 3-methoxyphenyl 4-(hydroxymethyl)benzoate were dissolved in 100 mL of chloroform and 2.85 mL (3 eq) of 3-(triethoxysilyl)propyl isocyanate and 1.60 mL (3 eq) of triethylamine were added. The resulting solution was refluxed for 48 hours. Once cooled to room temperature again, the solvent was evaporated under reduced pressure and the excess of reactants were distilled at vacuum, yielding the desired product as an oil (quantitative yield).

¹H-NMR (CDCl₃): 8.20 ppm (d, 2H), 7.50 ppm (d, 2H), 7.34 ppm (t, 1H), 6.84 ppm (td, 2H), 6.78 ppm (t, 1H), 4.8 ppm (s, 2H), 3.83 ppm (s, 3H), 3.20 ppm (t, 2H), 1.61 ppm (m, 2H), 1.23 ppm (t, 9H), 0.69 ppm (m, 2H)

Example 4. Synthesis of 3-(diethylamino)phenyl 4-((3-(triethoxysilyl)propylimino)methyl)benzoate (Compound 4)

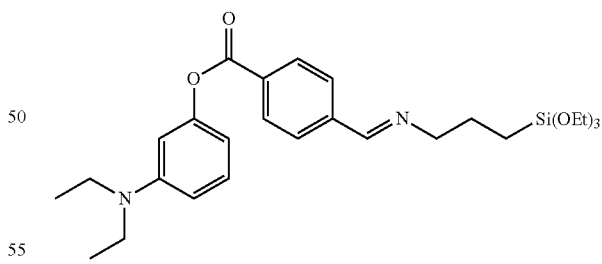

Step 1: Synthesis of 4-formylbenzoyl chloride 0.92 g (6.13 mmol) of 4-formylbenzoic acid were suspended in 50 mL of anhydrous toluene. 16 mL of thionyl chloride (0.22 mol) were added and the resulting suspension was heated at 130° C. for 3 hours under nitrogen atmosphere, then cooled to room temperature and the solvent evaporated under reduced pressure. 50 extra mL of toluene were added and evaporated under reduced pressure to eliminate possible remaining thionyl chloride. This process was repeated twice. The solid obtained was used immediately without further purification.

Step 2: Synthesis of 3-(diethylamino)phenyl 4-formylbenzoate 1.01 g (6.13 mmol) of 3-(diethylamino)phenol were suspended in 50 mL of dichloromethane and solubilized by adding 0.85 mL (6.13 mmol) of triethylamine. The resulting solution was stirred for 30 minutes and after this time a solution containing 4-formylbenzoyl chloride in dichloromethane (6.13 mmol of acyl chloride in 20 mL of solvent) was added dropwise. The resulting solution was stirred at room temperature for 5 hours, then extracted with saturated aqueous solution of sodium carbonate (3×40 mL), dried over magnesium sulfate and the solvent evaporated under reduced pressure. The brownish solid obtained was recrystallized with cyclohexane, yielding a yellowish solid (50% yield, 95% purity assessed by HPLC).

$^1$H-NMR (CDCl$_3$): 10.15 ppm (s, 1H), 8.37 ppm (d, 2H), 8.02 ppm (d, 2H), 7.24 ppm (t, 1H), 6.57 ppm (dd, 1H), 6.47 ppm (m, 2H), 3.35 ppm (q, 4H), 1.23 ppm (t, 6H)

Step 3: Synthesis of 3-(diethylamino)phenyl 4-((3-(triethoxysilyl)propylimino)methyl)benzoate 50 mg (0.17 mmol) of 3-(diethylamino)phenyl 4-formylbenzoate were suspended in 20 mL of chloroform and 37 mg (0.17 mmol) of 3-(aminopropyl)triethoxysilane were added, followed by the addition of 100 mg of anhydrous magnesium sulfate. The resulting suspension was stirred for 24 h at room temperature under nitrogen atmosphere. The crude was filtered and the solvent was eliminated under reduced pressure to yield an orange oil (quantitative yield).

$^1$H-NMR (CDCl$_3$): 8.36 ppm (s, 1H), 8.24 ppm (d, 2H), 7.85 ppm (d, 2H), 7.21 ppm (t, 1H), 6.57 ppm (dd, 1H), 6.47 ppm (m, 2H), 3.84 ppm (q, 6H), 3.67 ppm (t, 2H), 3.35 ppm (q, 4H), 1.86 ppm (m, 2H), 1.23 ppm (t, 9H), 1.17 ppm (t, 6H), 0.69 ppm (m, 2H).

Example 5. Synthesis of 3-(dimethylamino)phenyl 4-((3-(triethoxysilyl)propylimino)methyl)benzoate (Compound 5)

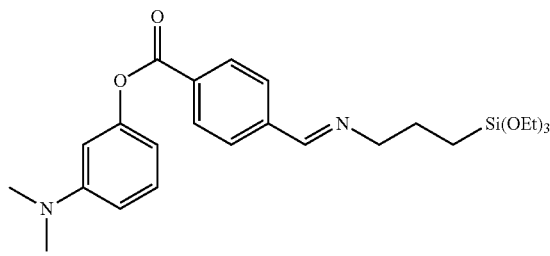

Step 1: Synthesis of 4-formylbenzoyl chloride 0.92 g (6.13 mmol) of 4-formylbenzoic acid were suspended in 50 mL of anhydrous toluene. 16 mL of thionyl chloride (0.22 mol) were added and the resulting suspension was heated at 130° C. for 3 hours under nitrogen atmosphere, then cooled to room temperature and the solvent evaporated under reduced pressure. 50 extra mL of toluene were added and evaporated under reduced pressure to eliminate possible remaining thionyl chloride. This process was repeated twice. The solid obtained was used immediately without further purification.

Step 2: Synthesis of 3-(dimethylamino)phenyl 4-formylbenzoate 0.84 g (6.13 mmol) of 3-(dimethylamino)phenol were suspended in 50 mL of dichloromethane and solubilized by adding 0.85 mL (6.13 mmol) of triethylamine. The resulting solution was stirred for 30 minutes and after this time a solution containing 4-formylbenzoyl chloride in dichloromethane (6.13 mmol of acyl chloride in 20 mL of solvent) was added dropwise. The resulting solution was stirred at room temperature for 5 hours, then extracted with saturated aqueous solution of sodium carbonate (3×40 mL), dried over magnesium sulfate and the solvent evaporated under reduced pressure. The brownish solid obtained was recrystallized with cyclohexane, yielding a yellowish solid (60% yield, 95% purity assessed by HPLC).

$^1$H-NMR (CDCl$_3$): 10.14 ppm (s, 1H), 8.37 ppm (d, 2H), 8.02 ppm (d, 2H), 7.26 ppm (t, 1H), 6.64 ppm (dd, 1H), 6.54 ppm (dd+t, 2H), 2.97 ppm (s, 6H)

Step 3: Synthesis of 3-(dimethylamino)phenyl 4-((3-(triethoxysilyl)propylimino)methyl)benzoate 50 mg (0.19 mmol) of 3-(dimethylamino)phenyl 4-formylbenzoate were suspended in 20 mL of chloroform and 41 mg (0.19 mmol) of 3-(aminopropyl)triethoxysilane were added, followed by the addition of 100 mg of anhydrous magnesium sulfate. The resulting suspension was stirred for 24 h at room temperature under nitrogen atmosphere. The crude was filtered and the solvent was eliminated under reduced pressure to yield an orange oil (quantitative yield).

$^1$H-NMR (CDCl$_3$): 8.36 ppm (s, 1H), 8.24 ppm (d, 2H), 7.85 ppm (d, 2H), 7.27 ppm (t, 1H), 6.63 ppm (dd, 1H), 6.55 ppm (m, 2H), 3.85 ppm (q, 6H), 3.67 ppm (t, 2H), 2.97 (s, 6H), 1.86 ppm (m, 2H), 1.23 ppm (t, 9H), 0.70 ppm (m, 2H).

Example 6. Synthesis of 3-methoxyphenyl 4-((3-(triethoxysilyl)propylimino)methyl)benzoate (Compound 6)

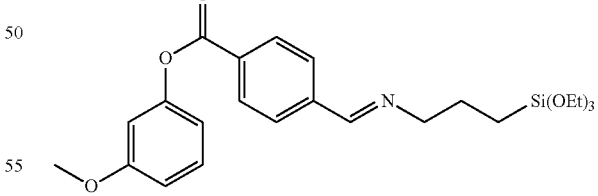

Step 1: Synthesis of 4-formylbenzoyl chloride 0.92 g (6.13 mmol) of 4-formylbenzoic acid were suspended in 50 mL of anhydrous toluene. 16 mL of thionyl chloride (0.22 mol) were added and the resulting suspension was heated at 130° C. for 3 hours under nitrogen atmosphere, then cooled to room temperature and the solvent evaporated under reduced pressure. 50 extra mL of toluene were added and evaporated under reduced pressure to eliminate nate possible remaining thionyl chloride. This process was repeated twice. The solid obtained was used immediately without further purification.

Step 2: Synthesis of 3-methoxyphenyl 4-formylbenzoate 0.76 g (6.13 mmol) of 3-methoxyphenol were suspended in 50 mL of dichloromethane and solubilized by adding 0.85 mL (6.13 mmol) of triethylamine. The resulting solution was stirred for 30 minutes and after this time a solution containing 4-formylbenzoyl chloride in dichloromethane (6.13 mmol of acyl chloride in 20 mL of solvent) was added dropwise. The resulting solution was stirred at room temperature for 5 hours, then extracted with saturated aqueous solution of sodium carbonate (3×40 mL), dried over magnesium sulfate and the solvent evaporated under reduced pressure. A white solid was obtained with a 96% of purity, as assessed by HPLC (90% yield).
$^1$H-NMR (CDCl$_3$): 10.14 ppm (s, 1H), 8.37 ppm (d, 2H), 8.02 ppm (d, 2H), 7.34 ppm (t, 1H), 6.84 ppm (td, 2H), 6.78 ppm (t, 1H), 3.83 ppm (s, 3H)

Step 3: Synthesis of 3-methoxyphenyl 4-((3-(triethoxysilyl)propylimino)methyl)benzoate 50 mg (0.20 mmol) of 3-methoxyphenyl 4-formylbenzoate were suspended in 20 mL of chloroform and 43 mg (0.20 mmol) of 3-(aminopropyl)triethoxysilane were added, followed by the addition of 100 mg of anhydrous magnesium sulfate. The resulting suspension was stirred for 24 h at room temperature under nitrogen atmosphere. The crude was filtered and the solvent was eliminated under reduced pressure to yield an orange oil (quantitative yield).
$^1$H-NMR (CDCl$_3$): 8.36 ppm (s, 1H), 8.24 ppm (d, 2H), 7.85 ppm (d, 2H), 7.32 ppm (t, 1H), 6.83 ppm (m, 2H), 6.79 ppm (t, 1H), 3.83 ppm (q+s, 6H+3H OMe), 3.67 ppm (t, 2H), 1.86 ppm (m, 2H), 1.23 ppm (t, 9H), 0.70 ppm (m, 2H).

Example 7. Preparation of Particles 7.1. Particle Characterization
The particles obtained according to the processes described below were characterized by size distribution, UV-Vis spectroscopy and HPLC chromatography.
7.1.1. Particle Morphology
Size distribution shows that particles are monodisperse with size 370±70 nm.
7.1.2. UV-Vis Spectroscopy
A suspension of particles 3% (30 mg/mL) in PEG-300 was added to a PMMA plate at a rate of 1.3 mg/cm$^2$. Particles show an intense absorption in UVB region with a queue going to UVA when the UV-Vis spectrum was registered with an integrating sphere in diffuse transmittance mode.
7.1.3. HPLC Chromatography
Particles hermeticity was determined by extraction with solvents at high temperature, the extracts being analyzed by HPLC. Particles (200 mg) and 100 mL of a mixture of methanol and water ((80:20) were refluxed in a Soxhlet for 5 hours. Solvent samples were analyzed by HPLC under the following conditions:
Equipment: HP 1090 Liquid Chromatograph
Column: Reverse Phase Kromasil C18 5 µm 15×0.46
Mobile Phase: acetonitrile/water 80:20
Flow: 1.0 mL/min
Detection: absorption 254 nm Particles chromatogram showed only a solvent dead point time, thus indicating that particles are essentially hermetic.
7.2. Particles Phototransformation
Particles, suspended in PEG-300, were irradiated at 35° C. in a Luzchem ICH-2 photoreactor provided with 16 UVB lamps (irradiance 70 W/m$^2$).
7.2.1. UV-Vis Spectroscopy
The 3% particles suspension in PEG-300 was added to a PMMA plate at a rate of 1.3 mg/cm$^2$. The evolution of photoconversion was controlled by measuring the diffuse transmitance of the sample between 280 and 400 nm.
Particles spectrum shows the irradiated particles absorb both in UVB and UVA regions.
7.2.2. HPLC Chromatography
HPLC chromatography of irradiated microcapsules was performed in the same way as for non-irradiated microcapsules (2.4).
Particles chromatogram showed only a solvent dead point time, thus indicating that particles are essentially hermetic.
7.3. Preparation of Particles:
3-(diethylamino)phenyl 4-((3-(triethoxysilyl)propylimino)methyl)benzoate particles (P1);
3-(diethylamino)phenyl 4-((3-(triethoxysilyl)propylcarbamoyloxy)methyl)benzoate particles (P2);
3-(dimethylamino)phenyl 4-((3-(triethoxysilyl)propylcarbamoyloxy)methyl)benzoate particles (P3);
3-methoxyphenyl 4-((3-(triethoxysilyl)propylcarbamoyloxy)methyl)benzoate particles (P4);
3-(dimethylamino)phenyl 4-((3-(triethoxysilyl)propylimino)methyl)benzoate particles (P5);
3-methoxyphenyl 4-((3-(triethoxysilyl)propylimino)methyl)benzoate particles (P6)

Particles P1 were prepared as follows: A mixture of ethanol (3.8 mL, 0.082 mmol) and deionized water (1.4 mL, 0.078 mmol) was heated in a water bath to 40° C. with stirring. A mixture of tetraethoxy silane, (TEOS, 396 mg, 1.903 mmol), and 3-(diethylamino)phenyl 4-((3-(triethoxysilyl)propylimino)methyl)benzoate (150 mg, 0.326 mmol) was heated with no stirring in the same bath. When the ethanol/water mixture temperature attained 40° C., 1.7 mL of 30% of ammonia (0.011 mmol) were added and the stirring was augmented to assure a homogenous mixture. When the temperature attained again 40° C., the solution of TEOS and 3-(3-(triethoxysilyl)propoxy)phenyl benzoate was added and stirred for 15 seconds. The resultant suspension was allowed to stay for 1 hour at 40° C., thus centrifugated and washed with water (25 mL×3). Finally, the particles were resuspended in an aqueous solution containing 0.5% w/w of PVP k-90 and HPMC as stabilisers. The content of chromophore in the particles was 50% w/w, expressed as 3-(diethylamino)phenyl 4-methylbenzoate.

Particles P2-P6 were prepared from appropriate reagents following the synthesis described above. HPLC hermeticity was assessed for all compounds. Preparative and analytical details are summarized in Table 1.

TABLE 1

| Ex. | Reactants mg (mmol) | | Ammonia 30% mL | Precursor percentage | Particles diameter nm |
|---|---|---|---|---|---|
| | TEOS | Monomer | | | |
| 2 | 396 (1.903) | 150 (0.326) | 1.7 | 51 (1) | 320 ± 30 |
| 3 | 396 (1.903) | 150 (0.326) | 1.7 | 51 (2) | 410 ± 50 |

TABLE 1-continued

| | Reactants mg (mmol) | | Ammonia 30% mL | Precursor percentage | Particles diameter nm |
|---|---|---|---|---|---|
| Ex. | TEOS | Monomer | | | |
| 4 | 396 (1.903)) | 150 (0.326) | 1.7 | 51 (3) | 340 ± 60 |
| 5 | 396 (1.903) | 150 (0.326) | 1.7 | 50 (4) | 370 ± 45 |
| 6 | 396 (1.903) | 150 (0.326) | 1.7 | 50 (5) | 420 ± 30 |

(1) expressed as 3-(diethylamino)phenyl 4-methylbenzoate
(2) expressed as 3-(dimethylamino)phenyl 4-methylbenzoate
(3) expressed as 3-methoxyphenyl 4-methylbenzoate
(4) expressed as 3-(dimethylamino)phenyl 4-methylbenzoate
(5) expressed as 3-methoxyphenyl 4-methylbenzoate Example 8. Preparation of a Sunscreen Composition A sunscreen composition was prepared with particles P1 as active ingredient.

The components of the composition are shown in the following table:

| Phase A | | Phase B | |
|---|---|---|---|
| Deionized water | 60.0% | Active ingredient | 8.75% |
| Disodium EDTA | 0.10% | Octyl salicylate | 5% |
| Glycerin | 1.5% | Aluminum stearate | 5% |
| NaCl | 3.0% | Cyclomethicone + Dimethicone | 10% |
| Butylene glycol | 2.5% | Cetyl dimethicone | 1% |
| | | Cyclomethicone | 2% |
| | | ABIC-EM 97 | 1% |
| | | Fragrance | 0.15% |
| | TOTAL | | 100.00% |

Phase B ingredients were combined. The mixture was stirred and heated to 70-75° C. Phase A ingredients were combined. The mixture was heated to 70-75° C. while stirring. Phase B was added to phase A while stirring. Preservative was added. The mixture was stirred, allowing to cool to room temperature.

Example 9 Comparative. Study of the Phototransformation of 3-methoxyphenyl 4-((3-(triethoxysilyl)propylimino)methyl)benzoate (Compound 6) and 3-(3-(triethoxysilyl)propyloxy)phenyl benzoate The phototransformation rate of precursor 3-methoxyphenyl 4-((3-(triethoxysilyl)propylimino)methyl)benzoate (Compound 6 of the present invention) was compared to that of the precursor 3-(3-(triethoxysilyl)propyloxy)phenyl benzoate described in the prior art (comparative compound A).

Figure 7:
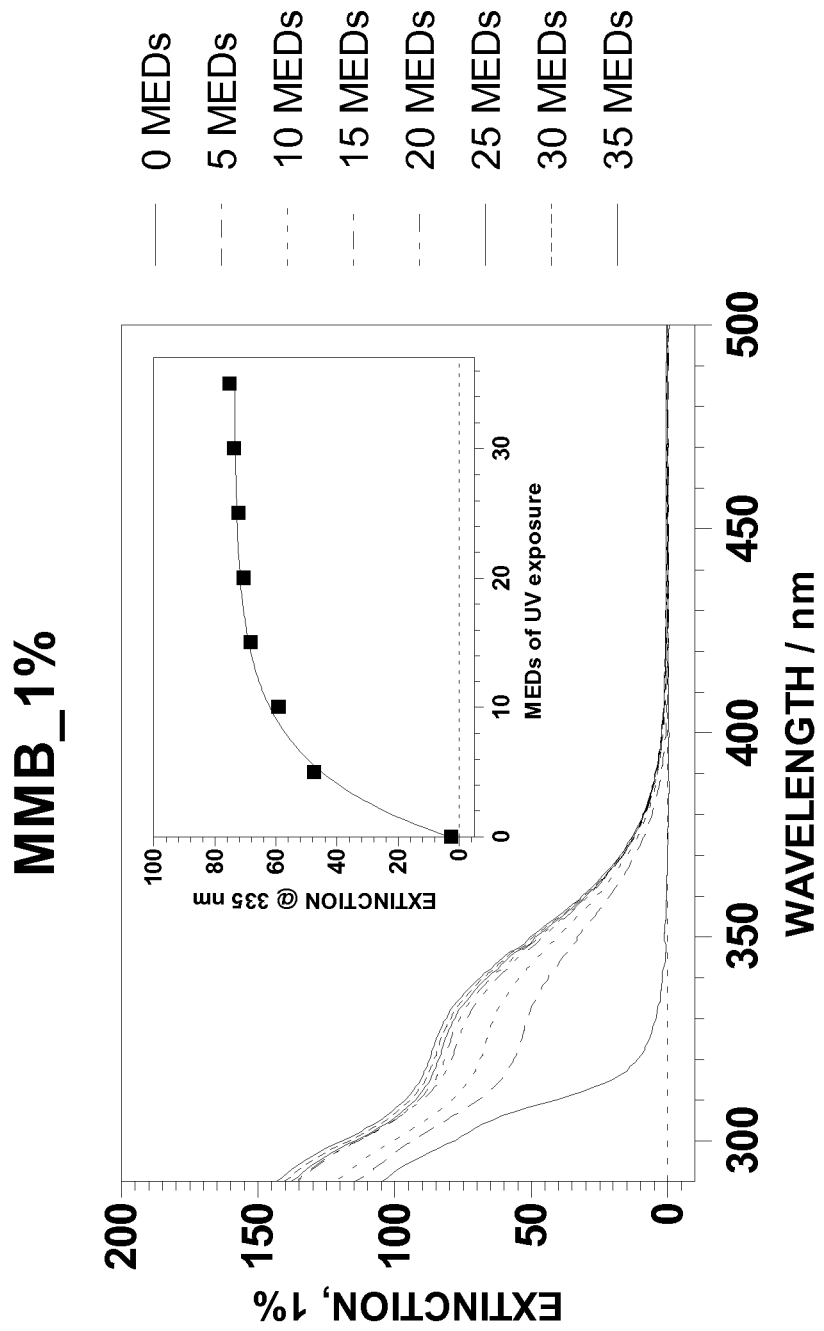
FIG. 7 shows the phototransformation kinetics of precursor 3-methoxyphenyl 4-((3-(triethoxysilyl)propylimino) methyl)benzoate (compound 6).
Figure 8:
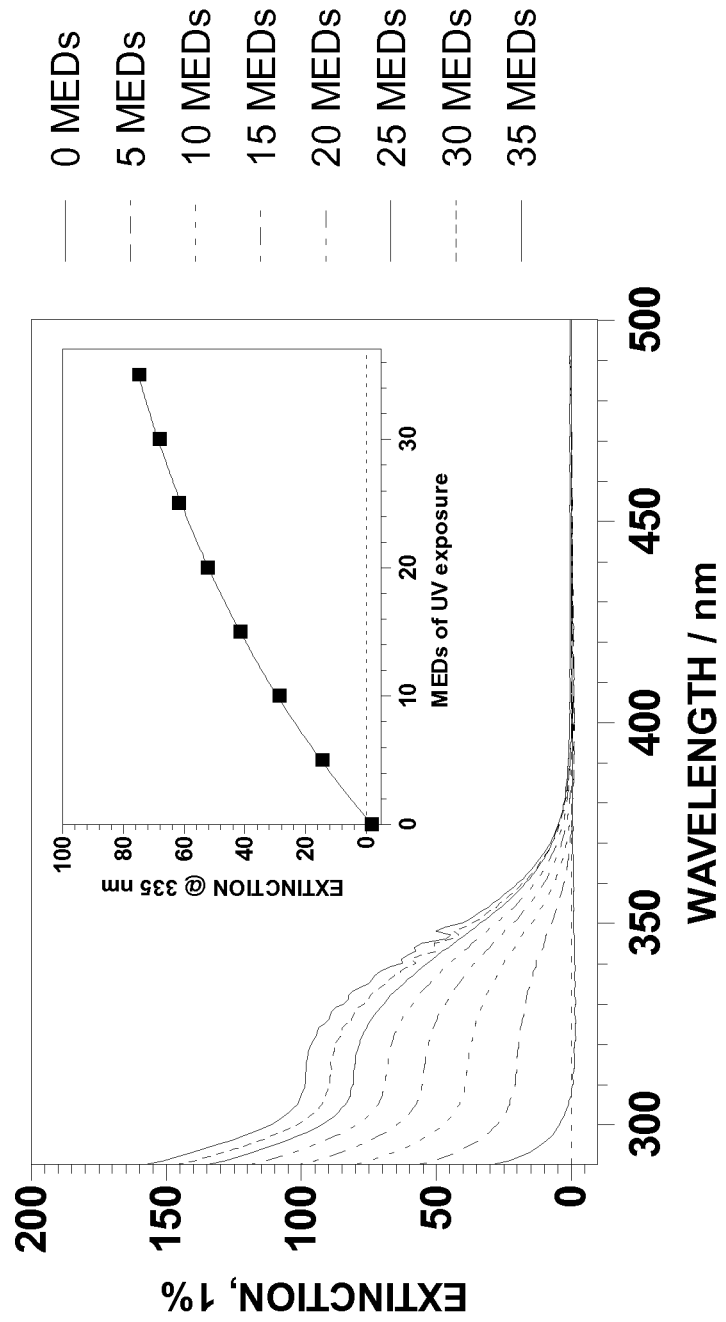
FIG. 8 shows the phototransformation kinetics of precursor 3-(3-(triethoxysilyl)propyloxy)phenyl benzoate (comparative compound A).

These precursors were dissolved in ethanol at a concentration of 1% w/v (10 mg/L) and exposed to simulated solar radiation in a SUNTEST ATLAS XLS+ equipped with a daylight filter (290-800 nm, 765 W/m$^2$). FIG. 7 and FIG. 8 show the phototransformation extent of compound 6 of the invention and comparative compound A, respectively. The insets in each graph show the phototransformation kinetics at 335 nm.

The following table shows the final extinction value of each precursor after being exposed to simulated solar radiation, as well as the half-life of the transformation ($t_{50}$, the number of MEDs needed to reach 50% of the final extinction value).

| Precursor | Final extinction value at 335 nm | $t_{50}$/MEDs |
|---|---|---|

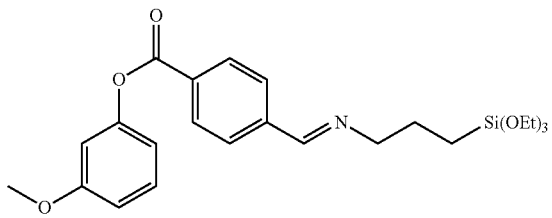

| | 75 | 3.5 |

Compound 6

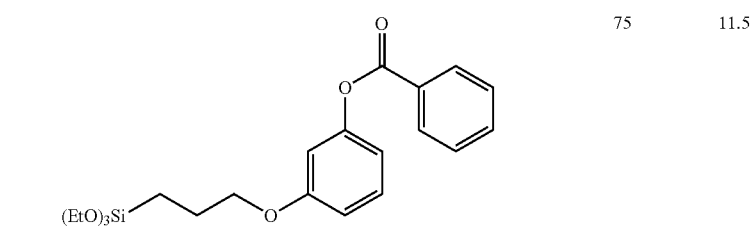

| | 75 | 11.5 |

Comparative compound A

As can be observed, transformation of compound 6 is 3.3-fold faster than that of comparative compound A. Thus, introduction of the silylated chain on the acyl ring accelerates its phototransformation.

Example 10 Comparative. Study of the Phototransformation of 3-(diethylamino)phenyl 4-((3-(triethoxysilyl)propylcarbamoyloxy)methyl)benzoate (Compound 1) and 3-(bis(3-(triethoxysilyl)propyl)amino)phenyl benzoate (Comparative Compound B)

The phototransformation rate of precursor 3-(diethylamino)phenyl 4-((3-(triethoxysilyl)propylcarbamoyloxy)methyl)benzoate (Compound 1 of the present invention) was compared to that of the precursor 3-(bis(3-(triethoxysilyl)propyl)amino)phenyl benzoate described in the prior art (comparative compound B).

Figure 9:
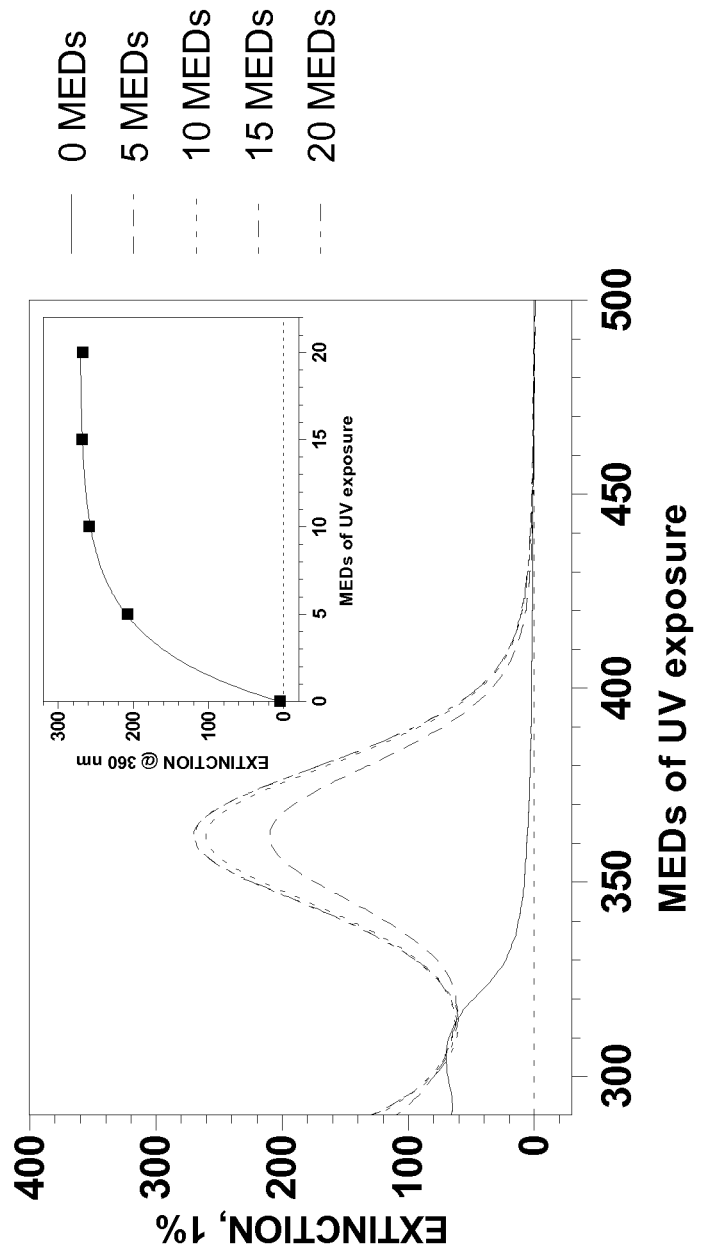
FIG. 9 shows the phototransformation kinetics of precursor 3-(diethylamino)phenyl 4-((3-(triethoxysilyl)propylcarbamoyloxy) methyl)benzoate (compound 1).
Figure 10:
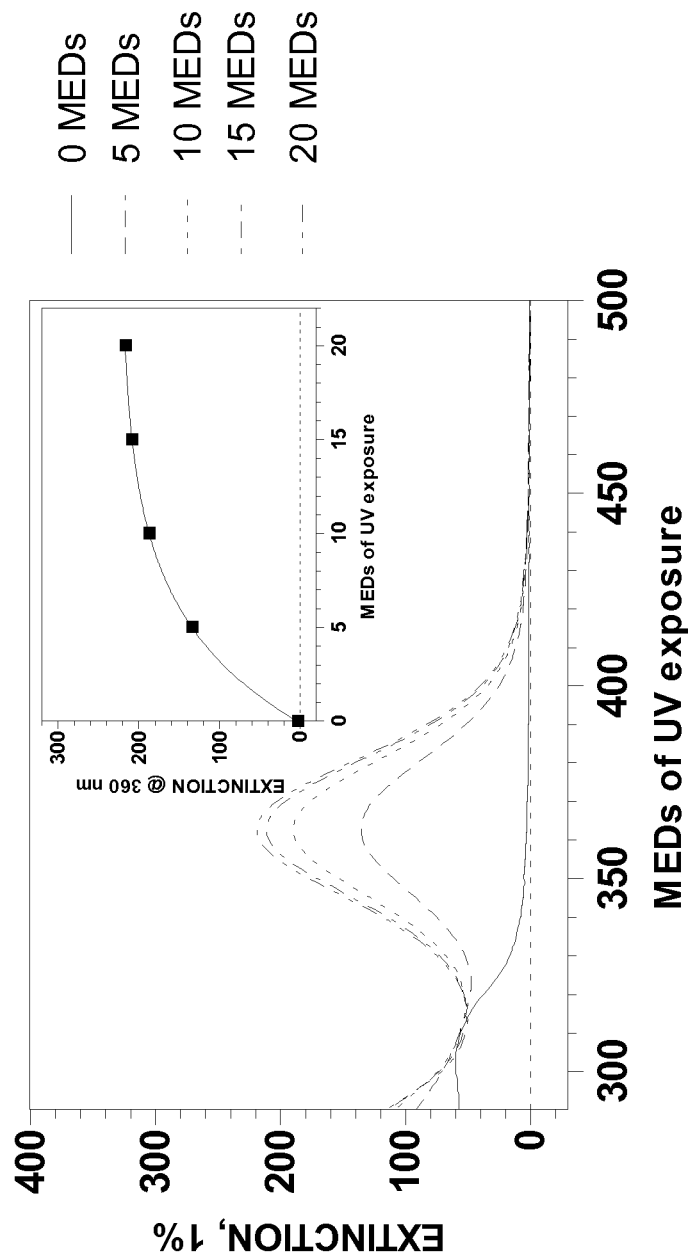
FIG. 10 shows the phototransformation kinetics of precursor 3-(bis(3-(triethoxysilyl)propyl)amino)phenyl benzoate (comparative compound B)

These precursors were dissolved in ethanol at a concentration of 1% w/v (10 mg/L) and exposed to simulated solar radiation in a SUNTEST ATLAS XLS+ equipped with a daylight filter (290-800 nm, 765 W/m$^2$). FIG. 9 and FIG. 10 show the phototransformation extent of compound 1 of the invention and comparative compound B, respectively. The insets in each graph show the phototransformation kinetics at 360 nm.

The following table shows the final extinction values that each precursor achieves after being exposed to simulated solar radiation, as well as the parameter $t_{50}$ which stands for the MEDs (minimal erythemal dose) of irradiation dose needed for each precursor to reach 50% of the final extinction value.

From the results quoted above, it can be concluded that introduction of the silylated chain on the acyl ring provides both a 22% higher increase of extinction after transformation and a 60% faster conversion rate.

Example 11 Comparative. Phototransformation of 3-methoxyphenyl 4-((3-(triethoxysilyl)propylimino)methyl)benzoate (Compound 6) and 3-(3-(triethoxysilyl)propyloxy)phenyl benzoate (Comparative Compound A) in the Presence of Additional Commercial Sunscreens An ethanolic solution (a) containing the commercial UV filters Tinosorb-S (3.7 mg/L) and 4-MBC (4.9 mg/L), and compound 6 of the invention (10 mg/L) was prepared. For comparative purposes, an ethanolic solution (b) containing the commercial UV filters Tinosorb-S (3.7 mg/L) and 4-MBC (4.9 mg/L), and comparative compound A (10 mg/L) was also prepared.

Both solutions were exposed to simulated solar radiation in a SUNTEST ATLAS XLS+ equipped with a daylight filter (290-800 nm, 765 W/m$^2$).

Figure 11:
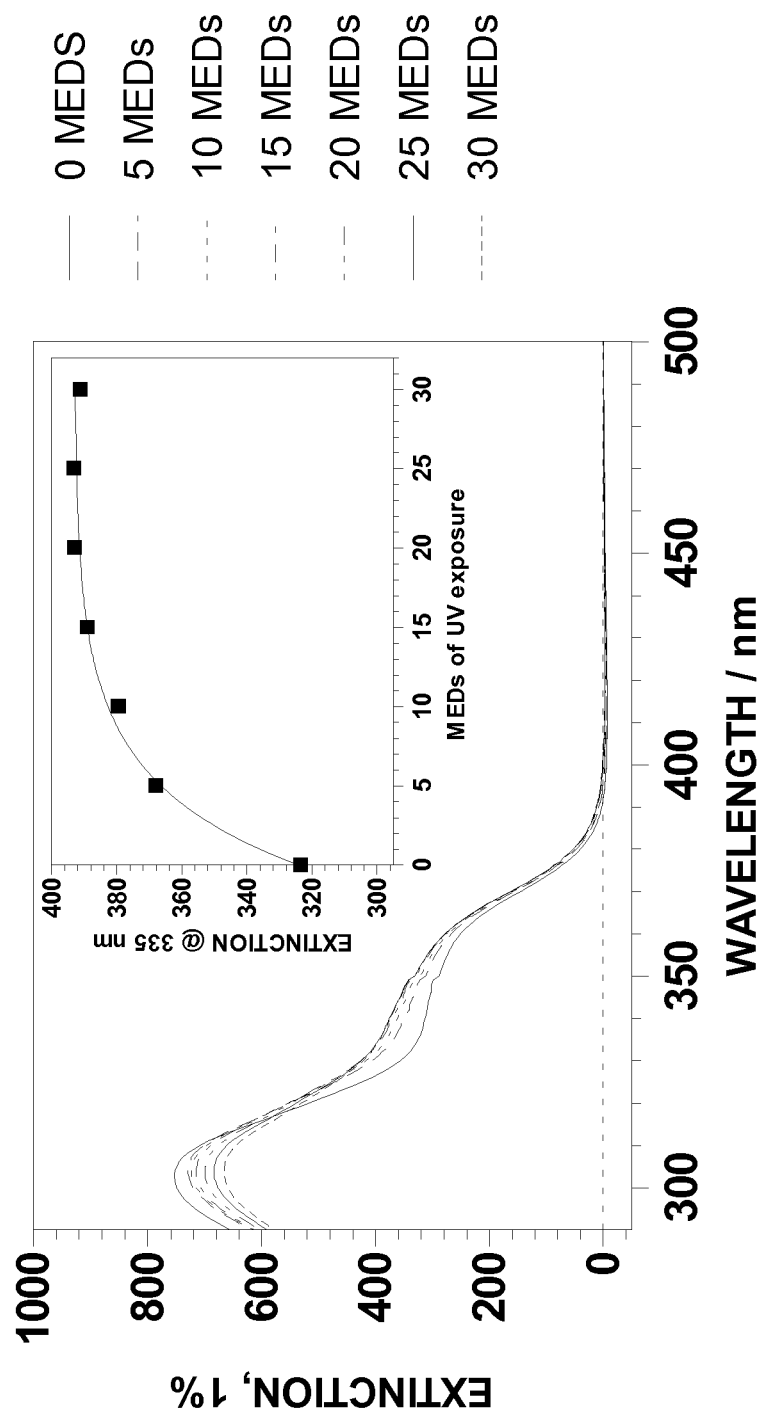
FIG. 11 shows the phototransformation kinetics of precursor 3-methoxyphenyl 4-((3-(triethoxysilyl)propylimino) methyl)benzoate (compound 6) in the presence of additional UV filters.
Figure 12:
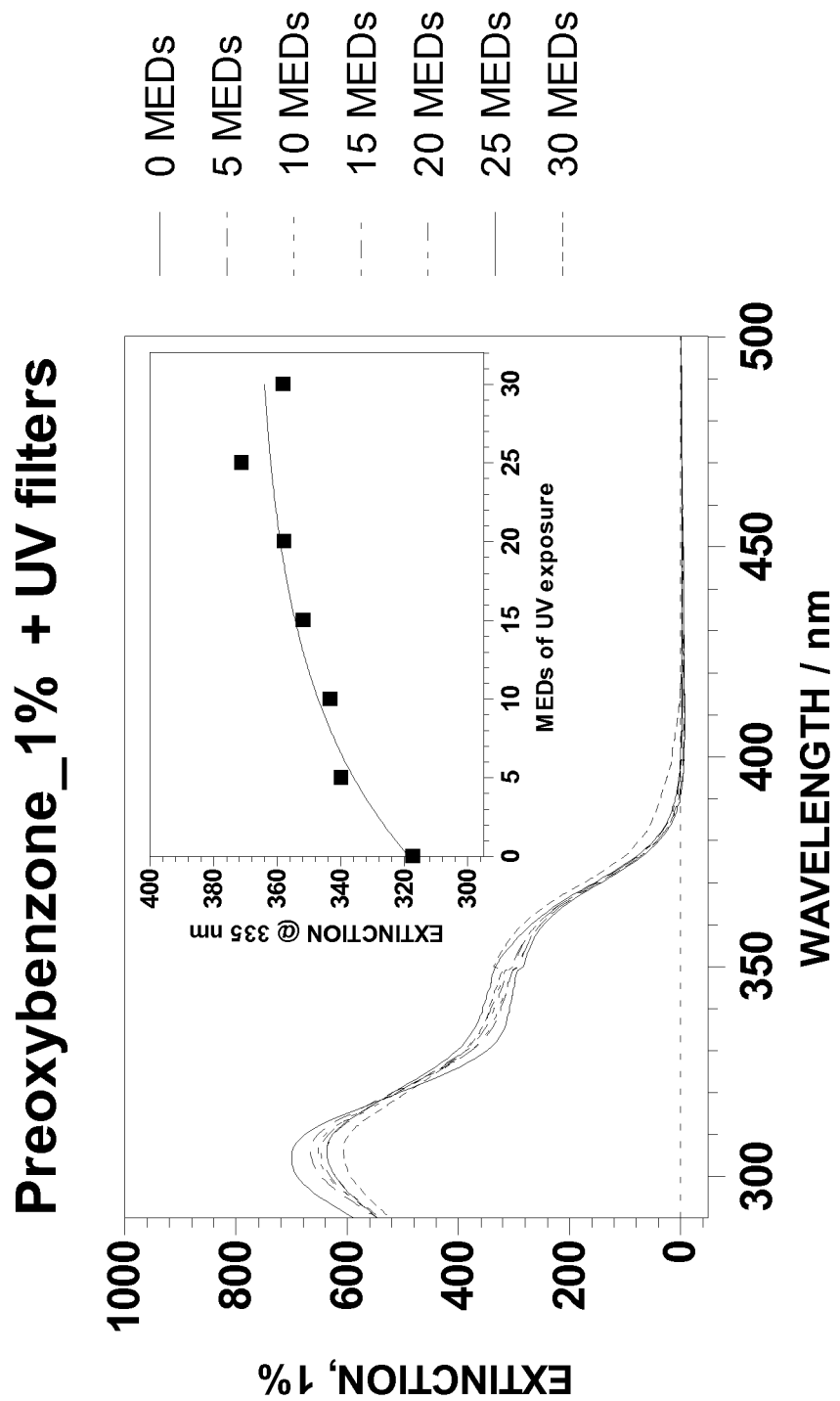
FIG. 12 shows the phototransformation kinetics of precursor 3-(3-(triethoxysilyl)propyloxy)phenyl benzoate (comparative compound A) in the presence of additional UV filters.

FIGS. 11 and 12 show the absorption spectra of both solutions (a) and (b), respectively. It can be observed that the final value of extinction at 335 nm is higher for the formulation containing compound 6 than in the formulation that contains comparative compound A. Consequently, it can be concluded that the introduction of the silylated chain on the acyl ring provides a precursor with a better ability to increase its sunscreening action in the presence of additional UV-filters.

| Precursor | Final extinction value at 360 nm | $t_{50}$/MEDs |
|---|---|---|
| 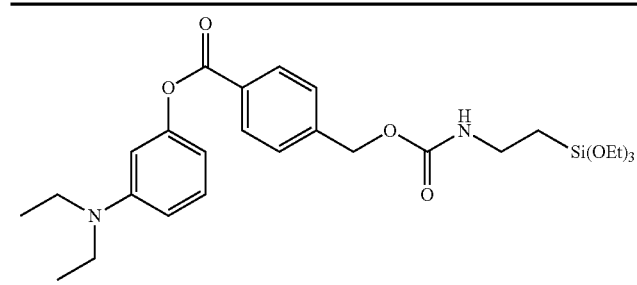 Compound 1 | 270 | 2.2 |
| 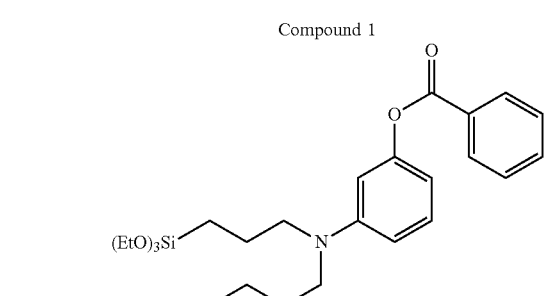 Comparative compound B | 220 | 3.5 |

Example 12 Comparative. Phototransformation of 3-(diethylamino)phenyl 4-((3-(triethoxysilyl)propyl-carbamoyloxy)methyl)benzoate (Compound 1) and 3-(bis(3-(triethoxysilyl)propyl)amino)phenyl benzoate (Comparative Compound B) in the Presence of Additional Commercial Sunscreens An ethanolic solution (c) containing the commercial UV filters Tinosorb-S (3.7 mg/L) and 4-MBC (4.9 mg/L), and compound 1 of the invention (10 mg/L) was prepared. For comparative purposes, an ethanolic solution (d) containing the commercial UV filters Tinosorb-S (3.7 mg/L) and 4-MBC (4.9 mg/L), and comparative compound B (10 mg/L) was also prepared.

Figure 13:
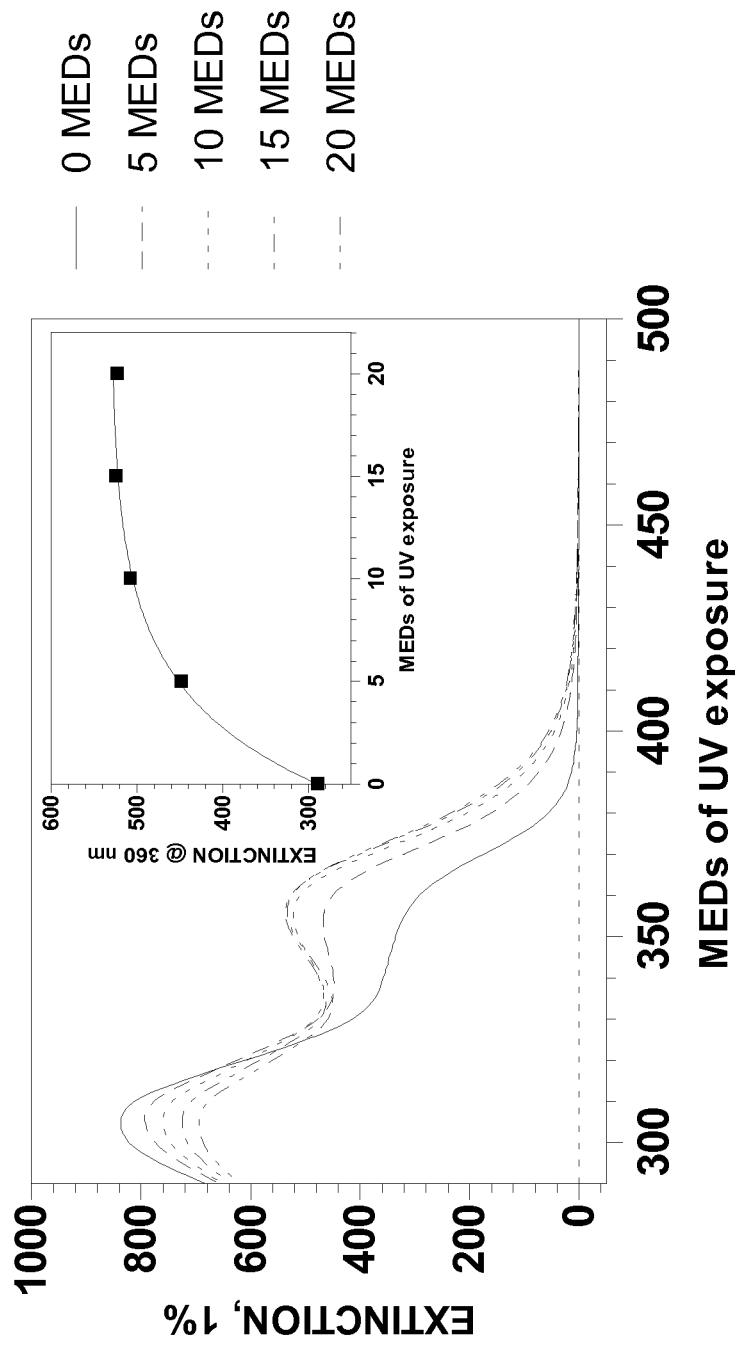
FIG. 13 shows the phototransformation kinetics of precursor 3-(diethylamino)phenyl 4-((3-(triethoxysilyl)propylcarbamoyloxy) methyl)benzoate (compound 1) in the presence of additional UV filters.
Figure 14:
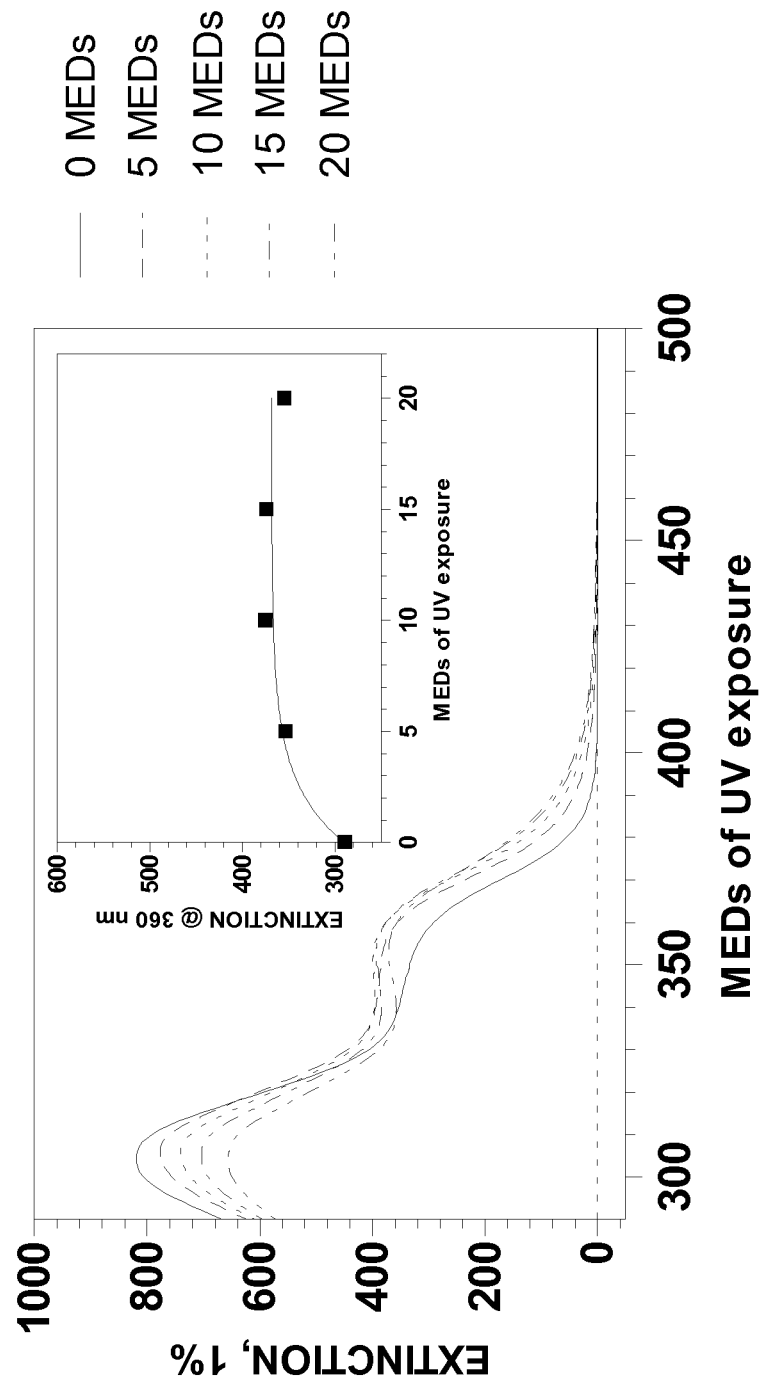
FIG. 14 shows the phototransformation kinetics of precursor 3-(bis(3-(triethoxysilyl)propyl)amino)phenyl benzoate (comparative compound B) in the presence of additional UV filters.

Both solutions were exposed to simulated solar radiation in a SUNTEST ATLAS XLS+ equipped with a daylight filter (290-800 nm, 765 W/m$^2$). FIGS. 13 and 14 show the absorption spectra of both solutions (c) and (d), respectively.

It can be observed that the final value of extinction at 365 nm is higher for the formulation containing the compound 1, while in the formulation containing comparative compound B the extinction at 365 nm remains almost constant after 20 MEDs of irradiation. Consequently, it can be concluded again that the introduction of the silylated chain on the acyl ring provides a precursor with a better ability to increase the protection in the UV-A region in the presence of additional UV-filters.

The invention claimed is:

1. A process for the preparation of an organosilicon progressive photoprotective polymer, which comprises the reaction of a monomer of formula (I):

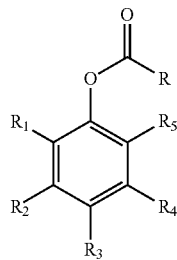

(I)

wherein:
R is selected from the group consisting of (i), (ii) and (iii):

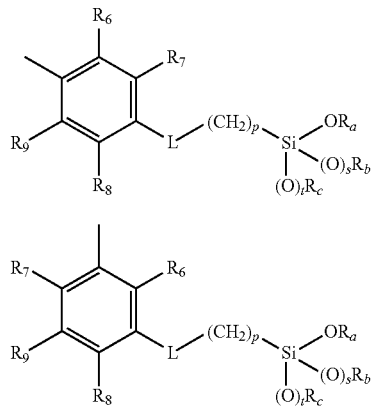

(i)

(ii)

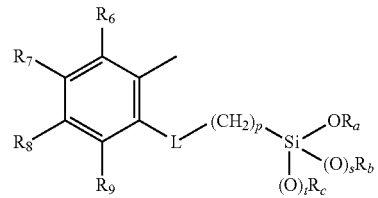

(iii)

wherein:
$R_1$, $R_2$, $R_3$, $R_4$ and $R_5$ are independently selected from the group consisting of H, linear or branched ($C_1$-$C_6$)alkyl, ($C_3$-$C_6$)cycloalkyl, $OR_{10}$, $NH_2$, $NHR_{11}$, $NR_{12}R_{13}$, COOH, $COOR_{14}$, $CONH_2$, $CONHR_{15}$, $CONR_{16}R_{17}$, $SO_2NH_2$, $SO_2NHR_{18}$, and $SO_2NR_{19}R_{20}$, with the proviso that at least one of $R_1$, $R_2$, $R_3$, $R_4$ and $R_5$ is not H provided that at least one of $R_1$ and $R_5$ is H;

$R_6$, $R_7$, $R_8$ and $R_9$ are independently selected from hydrogen, linear or branched ($C_1$-$C_6$)alkyl, ($C_3$-$C_6$)cycloalkyl, $OR'_1$, $NH_2$, $NHR'_2$ and $NR'_3R'_4$;

$R_{10}$ is linear or branched ($C_1$-$C_6$)alkyl or ($C_3$-$C_6$)cycloalkyl;

$R_{11}$ is linear or branched ($C_1$-$C_6$)alkyl or ($C_3$-$C_6$)cycloalkyl;

$R_{12}$ is linear or branched ($C_1$-$C_6$)alkyl or ($C_3$-$C_6$)cycloalkyl;

$R_{13}$ is linear or branched ($C_1$-$C_6$)alkyl or ($C_3$-$C_6$)cycloalkyl; or $R_{12}$ and $R_{13}$ taken together with the nitrogen atom to which they are attached form a pyrrolidine, piperidine or morpholine ring;

$R_{14}$ is linear or branched ($C_1$-$C_6$)alkyl or ($C_3$-$C_6$)cycloalkyl;

$R_{15}$ is linear or branched ($C_1$-$C_6$)alkyl or ($C_3$-$C_6$)cycloalkyl;

$R_{16}$ is linear or branched ($C_1$-$C_6$)alkyl or ($C_3$-$C_6$)cycloalkyl;

$R_{17}$ is linear or branched ($C_1$-$C_6$)alkyl or ($C_3$-$C_6$)cycloalkyl; or $R_{16}$ and $R_{17}$ taken together with the nitrogen atom to which they are attached form a pyrrolidine, piperidine or morpholine ring;

$R_{18}$ is linear or branched ($C_1$-$C_6$)alkyl or ($C_3$-$C_6$)cycloalkyl;

$R_{19}$ is linear or branched ($C_1$-$C_6$)alkyl or ($C_3$-$C_6$)cycloalkyl;

$R_{20}$ is linear or branched ($C_1$-$C_6$)alkyl or ($C_3$-$C_6$)cycloalkyl; or $R_{19}$ and $R_{20}$ taken together with the nitrogen atom to which they are attached form a pyrrolidine, piperidine or morpholine ring;

L is a linker selected from:
—CH═N—
(CH$_2$)—O—C(O)—NH—

$R_a$ is linear or branched ($C_1$-$C_6$)alkyl, linear or branched ($C_2$-$C_6$)alkenyl, ($C_3$-$C_6$)cycloalkyl or phenyl;

$R_b$ is linear or branched ($C_1$-$C_6$)alkyl, linear or branched ($C_2$-$C_6$)alkenyl, ($C_3$-$C_6$)cycloalkyl or phenyl;

$R_c$ is linear or branched ($C_1$-$C_6$)alkyl, linear or branched ($C_2$-$C_6$)alkenyl, ($C_3$-$C_6$)cycloalkyl or phenyl;

$R'_1$ is linear or branched ($C_1$-$C_6$)alkyl or ($C_3$-$C_6$)cycloalkyl;

$R'_2$ is linear or branched ($C_1$-$C_6$)alkyl or ($C_3$-$C_6$)cycloalkyl;

$R'_3$ is linear or branched ($C_1$-$C_6$)alkyl or ($C_3$-$C_6$)cycloalkyl;

$R'_4$ is linear or branched ($C_1$-$C_6$)alkyl or ($C_3$-$C_6$)cycloalkyl; or $R'_3$ and $R'_4$ taken together with the nitrogen atom to which they are attached form a pyrrolidine, piperidine or morpholine ring;

p is an integer selected from 2, 3 and 4;

s is an integer selected from 0 and 1;

t is an integer selected from 0 and 1;

with a compound of formula (IV):

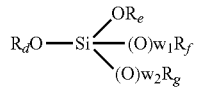 (IV)

wherein:

$R_d$ is a linear or branched ($C_1$-$C_6$)alkyl;

$R_e$, $R_f$ and $R_g$ are independently a linear or branched ($C_1$-$C_6$)alkyl, linear or branched ($C_2$-$C_6$)alkenyl, ($C_3$-$C_6$)cycloalkyl or phenyl, $w_1$ and $w_2$ are independently 0 or 1, in an alkanol/water mixture.

2. The process according to claim 1, further comprising a nitrogen-containing basic compound selected from the group consisting of ammonia, mono-alkylamine, di-alkylamine, tri-alkylamine, mono-alkanolamine, di-alkanolamine, and tri-alkanolamine, wherein both alkyl and alkanol groups are linear or branched having 1 to 6 carbon atoms.

3. The process according to claim 1, wherein the alkanol/water mixture is an ethanol/water mixture.

4. An organosilicon progressive photoprotective polymer obtainable by a process as defined in claim 1 comprising a micro- or nanoparticle form.

5. A method of preparing of a cosmetic or dermatological composition for protecting a human or animal living body from UV radiation comprising: mixing an organosilicon progressive photoprotective polymer as defined in claim 4 with cosmetic or dermatological ingredients to form the cosmetic or dermatological composition.

6. A method of making UV absorbers comprising obtaining a photoprotective polymer as defined in claim 4 as a photochemical precursor and forming the UV absorbers from the photoprotective polymer.

7. A method of protecting skin comprising: preparing a cosmetic or dermatological composition comprising a photoprotective polymer as defined in claim 4, applying the composition to human or animal living body, wherein the composition is effective to provide a progressive UV protection depending on the time to sun exposition and the degree of sun radiation.

8. A photoprotective polymer as defined in claim 4, which is effective in protecting a human or animal living body from UV radiation.

9. A cosmetic or dermatological composition comprising an organosilicon progressive photoprotective polymer as defined in claim 4 or a mixture thereof.

10. The cosmetic or dermatological composition according to claim 9, wherein the content of polymers ranges from 0.01% to 40% by weight, based on the total weight of the composition.

11. The cosmetic or dermatological composition according to claim 9, further comprising a sunscreen compound selected from avobenzone, 2-ethylhexyl-p-methoxycinnamate, oxybenzone, octyldimethyl p-aminobenzoic acid, dioxybenzone, ethyl-4-[bis(hydroxypropyl)]aminobenzoate, 2-ethylhexyl-2-cyan-3,3-diphenylacrylate, 2-ethylhexylsalicylate, glyceryl p-aminobenzoate, 3,3,5-trimethylcyclohexylsalicylate, methylanthranylate, p-dimethylaminobenzoic acid, 2-ethylhexyl p-dimethylaminobenzoate, 2-phenylbenzimidazole-5-sulfonic acid, 2-p-dimethylaminophenyl-5-sulfoniumbenzoxazoic acid, sulisobenzone, hexyl 2-(4-diethylamino-2-hidroxybenzoyl) benzoate, 2-(4-methylbenzyliden)-camphor, and 4-isopropyldibenzoylmethane.

12. A monomer of formula (I):

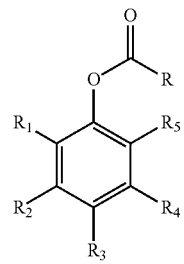 (I)

wherein:

R is selected from the group consisting of (i), (ii) and (iii):

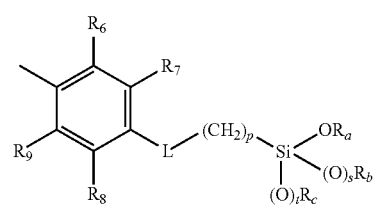 (i)

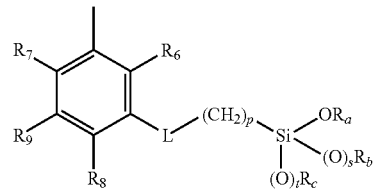 (ii)

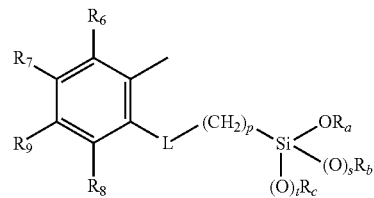 (iii)

wherein:

$R_1$, $R_2$, $R_3$, $R_4$ and $R_5$ are independently selected from the group consisting of H, linear or branched ($C_1$-$C_6$)alkyl, ($C_3$-$C_6$)cycloalkyl, $OR_{10}$, $NH_2$, $NHR_{11}$, $NR_{12}R_{13}$, COOH, $COOR_{14}$, $CONH_2$, $CONHR_{15}$, $CONR_{16}R_{17}$, $SO_2NH_2$, $SO_2NHR_{18}$, and $SO_2NR_{19}R_{20}$, with the proviso that at least one of $R_1$, $R_2$, $R_3$, $R_4$ and $R_5$ is not H provided that at least one of $R_1$ and $R_5$ is H;

$R_6$, $R_7$, $R_8$ and $R_9$ are independently selected from hydrogen, linear or branched ($C_1$-$C_6$)alkyl, ($C_3$-$C_6$)cycloalkyl, $OR'_1$, $NH_2$, $NHR'_2$ and $NR'_3R'_4$;

$R_{10}$ is linear or branched ($C_1$-$C_6$)alkyl or ($C_3$-$C_6$)cycloalkyl;

$R_{11}$ is linear or branched ($C_1$-$C_6$)alkyl or ($C_3$-$C_6$)cycloalkyl;

$R_{12}$ is linear or branched $(C_1-C_6)$alkyl or $(C_3-C_6)$cycloalkyl;

$R_{13}$ is linear or branched $(C_1-C_6)$alkyl or $(C_3-C_6)$cycloalkyl; or $R_{12}$ and $R_{13}$ taken together with the nitrogen atom to which they are attached form a pyrrolidine, piperidine or morpholine ring;

$R_{14}$ is linear or branched $(C_1-C_6)$alkyl or $(C_3-C_6)$cycloalkyl;

$R_{15}$ is linear or branched $(C_1-C_6)$alkyl or $(C_3-C_6)$cycloalkyl;

$R_{16}$ is linear or branched $(C_1-C_6)$alkyl or $(C_3-C_6)$cycloalkyl;

$R_{17}$ is linear or branched $(C_1-C_6)$alkyl or $(C_3-C_6)$cycloalkyl; or $R_{16}$ and $R_{17}$ taken together with the nitrogen atom to which they are attached form a pyrrolidine, piperidine or morpholine ring;

$R_{18}$ is linear or branched $(C_1-C_6)$alkyl or $(C_3-C_6)$cycloalkyl;

$R_{19}$ is linear or branched $(C_1-C_6)$alkyl or $(C_3-C_6)$cycloalkyl;

$R_{20}$ is linear or branched $(C_1-C_6)$alkyl or $(C_3-C_6)$cycloalkyl; or $R_{19}$ and $R_{20}$ taken together with the nitrogen atom to which they are attached form a pyrrolidine, piperidine or morpholine ring;

L is a linker selected from:

—CH=N— 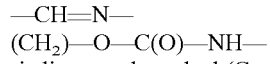

(CH$_2$)—O—C(O)—NH—

$R_a$ is linear or branched $(C_1-C_6)$alkyl, linear or branched $(C_2-C_6)$alkenyl, $(C_3-C_6)$cycloalkyl or phenyl;

$R_b$ is linear or branched $(C_1-C_6)$alkyl, linear or branched $(C_2-C_6)$alkenyl, $(C_3-C_6)$cycloalkyl or phenyl;

$R_c$ is linear or branched $(C_1-C_6)$alkyl, linear or branched $(C_2-C_6)$alkenyl, $(C_3-C_6)$cycloalkyl or phenyl;

$R'_1$ is linear or branched $(C_1-C_6)$alkyl or $(C_3-C_6)$cycloalkyl;

$R'_2$ is linear or branched $(C_1-C_6)$alkyl or $(C_3-C_6)$cycloalkyl;

$R'_3$ is linear or branched $(C_1-C_6)$alkyl or $(C_3-C_6)$cycloalkyl;

$R'_4$ is linear or branched $(C_1-C_6)$alkyl or $(C_3-C_6)$cycloalkyl; or $R'_3$ and $R'_4$ taken together with the nitrogen atom to which they are attached form a pyrrolidine, piperidine or morpholine ring;

p is an integer selected from 2, 3 and 4;

s is an integer selected from 0 and 1;

t is an integer selected from 0 and 1;

or enantiomeric forms, or cosmetically or dermatologically acceptable salts thereof.

13. A process for the preparation of a monomer of formula (I) according to claim 12, when L is a group CH=N—, which comprises the reaction of a compound of formula (II):

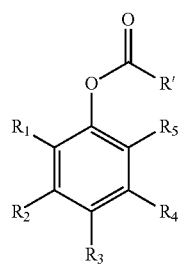

(II)

wherein:

$R_1$, $R_2$, $R_3$, $R_4$ and $R_5$ are independently selected from the group consisting of H, linear or branched $(C_1-C_6)$alkyl, $(C_3-C_6)$cycloalkyl, $OR_{10}$, $NH_2$, $NHR_{11}$, $NR_{12}R_{13}$, COOH, $COOR_{14}$, $CONH_2$, $CONHR_{15}$, $CONR_{16}R_{17}$, $SO_2NH_2$, $SO_2NHR_{18}$, and $SO_2NR_{19}R_{20}$, with the proviso that at least one of $R_1$, $R_2$, $R_3$, $R_4$ and $R_5$ is not H provided that at least one of $R_1$ and $R_5$ is H;

$R_{10}$ is linear or branched $(C_1-C_6)$alkyl or $(C_3-C_6)$cycloalkyl;

$R_{11}$ is linear or branched $(C_1-C_6)$alkyl or $(C_3-C_6)$cycloalkyl;

$R_{12}$ is linear or branched $(C_1-C_6)$alkyl or $(C_3-C_6)$cycloalkyl;

$R_{13}$ is linear or branched $(C_1-C_6)$alkyl or $(C_3-C_6)$cycloalkyl; or $R_{12}$ and $R_{13}$ taken together with the nitrogen atom to which they are attached form a pyrrolidine, piperidine or morpholine ring;

$R_{14}$ is linear or branched $(C_1-C_6)$alkyl or $(C_3-C_6)$cycloalkyl;

$R_{15}$ is linear or branched $(C_1-C_6)$alkyl or $(C_3-C_6)$cycloalkyl;

$R_{16}$ is linear or branched $(C_1-C_6)$alkyl or $(C_3-C_6)$cycloalkyl;

$R_{17}$ is linear or branched $(C_1-C_6)$alkyl or $(C_3-C_6)$cycloalkyl; or $R_{16}$ and $R_{17}$ taken together with the nitrogen atom to which they are attached form a pyrrolidine, piperidine or morpholine ring;

$R_{18}$ is linear or branched $(C_1-C_6)$alkyl or $(C_3-C_6)$cycloalkyl;

$R_{19}$ is linear or branched $(C_1-C_6)$alkyl or $(C_3-C_6)$cycloalkyl;

$R_{20}$ is linear or branched $(C_1-C_6)$alkyl or $(C_3-C_6)$cycloalkyl; or $R_{19}$ and $R_{20}$ taken together with the nitrogen atom to which they are attached form a pyrrolidine, piperidine or morpholine ring;

and

R' is selected from (i'), (ii') and (iii'):

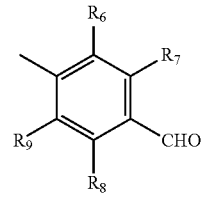

(i')

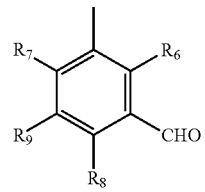

(ii')

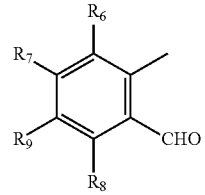

(iii')

wherein:
$R_6$, $R_7$, $R_8$ and $R_9$ are independently selected from hydrogen, linear or branched $(C_1\text{-}C_6)$alkyl, $(C_3\text{-}C_6)$cycloalkyl, $OR'_1$, $NH_2$, $NHR'_2$ and $NR'_3R'_4$;

with a compound of formula (III):

$$H_2N-(CH_2)_p-Si(OR_a)(O)_sR_b(O)_tR_c \quad (III)$$

wherein:
$R_a$ is linear or branched $(C_1\text{-}C_6)$alkyl, linear or branched $(C_2\text{-}C_6)$alkenyl, $(C_3\text{-}C_6)$cycloalkyl or phenyl;
$R_b$ is linear or branched $(C_1\text{-}C_6)$alkyl, linear or branched $(C_2\text{-}C_6)$alkenyl, $(C_3\text{-}C_6)$cycloalkyl or phenyl;
$R_c$ is linear or branched $(C_1\text{-}C_6)$alkyl, linear or branched $(C_2\text{-}C_6)$alkenyl, $(C_3\text{-}C_6)$cycloalkyl or phenyl;
p is an integer selected from 2, 3 and 4;
s is an integer selected from 0 and 1;
t is an integer selected from 0 and 1.

14. A process for the preparation of a monomer of formula (I) according to claim 12, when L is $CH_2\text{—}O\text{—}C(O)\text{—}NH\text{—}$, which comprises:

a) the reduction reaction of a compound of formula (II) as defined above, in the presence of a reducing agent, to produce a compound of formula (V):

$$\text{(V): aromatic ring with } R_1, R_2, R_3, R_4, R_5 \text{ substituents and } O\text{—}C(O)\text{—}R''$$

wherein:
$R_1$, $R_2$, $R_3$, $R_4$ and $R_5$ are independently selected from the group consisting of H, linear or branched $(C_1\text{-}C_6)$alkyl, $(C_3\text{-}C_6)$cycloalkyl, $OR_{10}$, $NH_2$, $NHR_{11}$, $NR_{12}R_{13}$, COOH, $COOR_{14}$, $CONH_2$, $CONHR_{15}$, $CONR_{16}R_{17}$, $SO_2NH_2$, $SO_2NHR_{18}$, and $SO_2NR_{19}R_{20}$, with the proviso that at least one of $R_1$, $R_2$, $R_3$, $R_4$ and $R_5$ is not H provided that at least one of $R_1$ and $R_5$ is H;
$R_{10}$ is linear or branched $(C_1\text{-}C_6)$alkyl or $(C_3\text{-}C_6)$cycloalkyl;
$R_{11}$ is linear or branched $(C_1\text{-}C_6)$alkyl or $(C_3\text{-}C_6)$cycloalkyl;
$R_{12}$ is linear or branched $(C_1\text{-}C_6)$alkyl or $(C_3\text{-}C_6)$cycloalkyl;
$R_{13}$ is linear or branched $(C_1\text{-}C_6)$alkyl or $(C_3\text{-}C_6)$cycloalkyl; or $R_{12}$ and $R_{13}$ taken together with the nitrogen atom to which they are attached form a pyrrolidine, piperidine or morpholine ring;
$R_{14}$ is linear or branched $(C_1\text{-}C_6)$alkyl or $(C_3\text{-}C_6)$cycloalkyl;
$R_{15}$ is linear or branched $(C_1\text{-}C_6)$alkyl or $(C_3\text{-}C_6)$cycloalkyl;
$R_{16}$ is linear or branched $(C_1\text{-}C_6)$alkyl or $(C_3\text{-}C_6)$cycloalkyl;
$R_{17}$ is linear or branched $(C_1\text{-}C_6)$alkyl or $(C_3\text{-}C_6)$cycloalkyl; or $R_{16}$ and $R_{17}$ taken together with the nitrogen atom to which they are attached form a pyrrolidine, piperidine or morpholine ring;
$R_{18}$ is linear or branched $(C_1\text{-}C_6)$alkyl or $(C_3\text{-}C_6)$cycloalkyl;
$R_{19}$ is linear or branched $(C_1\text{-}C_6)$alkyl or $(C_3\text{-}C_6)$cycloalkyl;
$R_{20}$ is linear or branched $(C_1\text{-}C_6)$alkyl or $(C_3\text{-}C_6)$cycloalkyl; or $R_{19}$ and $R_{20}$ taken together with the nitrogen atom to which they are attached form a pyrrolidine, piperidine or morpholine ring;

R" is selected from (i"), (ii") and (iii'):

(i") aromatic ring with $R_6$, $R_7$, $R_8$, $R_9$ substituents, a methyl group and $CH_2OH$ (ii") aromatic ring with $R_6$, $R_7$, $R_8$, $R_9$ substituents, a methyl group and $CH_2OH$ (iii") aromatic ring with $R_6$, $R_7$, $R_8$, $R_9$ substituents, a methyl group and $CH_2OH$ and b) the reaction of the compound of formula (V) as defined above with a compound of formula (VI):

$$OCN-(CH_2)_p-Si(OR_a)(O)_sR_b(O)_tR_c \quad (VI)$$

wherein:
$R_a$ is linear or branched $(C_1\text{-}C_6)$alkyl, linear or branched $(C_2\text{-}C_6)$alkenyl, $(C_3\text{-}C_6)$cycloalkyl or phenyl;
$R_b$ is linear or branched $(C_1\text{-}C_6)$alkyl, linear or branched $(C_2\text{-}C_6)$alkenyl, $(C_3\text{-}C_6)$cycloalkyl or phenyl;
$R_c$ is linear or branched $(C_1\text{-}C_6)$alkyl, linear or branched $(C_2\text{-}C_6)$alkenyl, $(C_3\text{-}C_6)$cycloalkyl or phenyl;
p is an integer selected from 2, 3 and 4;
s is an integer selected from 0 and 1;
t is an integer selected from 0 and 1.

* * * * *